(12) United States Patent
Abunassar

(10) Patent No.: US 9,814,610 B2
(45) Date of Patent: *Nov. 14, 2017

(54) STENT WITH ELONGATING STRUTS

(71) Applicant: Abbott Cardiovascular Systems Inc., Santa Clara, CA (US)

(72) Inventor: Chad Joseph Abunassar, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/156,668

(22) Filed: May 17, 2016

(65) Prior Publication Data

US 2016/0256300 A1 Sep. 8, 2016

Related U.S. Application Data

(63) Continuation of application No. 14/507,634, filed on Oct. 6, 2014, now Pat. No. 9,381,103.

(51) Int. Cl.
*A61F 2/06* (2013.01)
*A61F 2/915* (2013.01)
*A61F 2/89* (2013.01)
*A61F 2/844* (2013.01)

(52) U.S. Cl.
CPC .............. *A61F 2/915* (2013.01); *A61F 2/844* (2013.01); *A61F 2/89* (2013.01); *A61F 2002/91525* (2013.01); *A61F 2002/91566* (2013.01); *A61F 2002/91583* (2013.01); *A61F 2210/0004* (2013.01); *A61F 2210/0057* (2013.01); *A61F 2230/0004* (2013.01); *A61F 2250/0018* (2013.01); *A61F 2250/0029* (2013.01); *A61F 2250/0036* (2013.01); *A61F 2250/0067* (2013.01); *A61F 2250/0071* (2013.01)

(58) Field of Classification Search
CPC ............ A61F 2/915; A61F 2002/91508; A61F 2002/915; A61F 2/89; A61F 2002/91516; A61F 2002/91525; A61F 2002/91533
See application file for complete search history.

(56) References Cited

U.S. PATENT DOCUMENTS

| | | | | |
|---|---|---|---|---|
| 6,423,090 B1 * | 7/2002 | Hancock | ................... | A61F 2/91 623/1.15 |
| 6,626,935 B1 * | 9/2003 | Ainsworth | ................ | A61F 2/91 623/1.15 |
| 7,029,493 B2 * | 4/2006 | Majercak | ................... | A61F 2/91 606/194 |
| 7,637,935 B2 * | 12/2009 | Pappas | ....................... | A61F 2/91 623/1.12 |
| 7,758,627 B2 * | 7/2010 | Richter | ..................... | A61F 2/91 606/198 |
| 8,298,279 B2 * | 10/2012 | Clarke | ...................... | A61F 2/91 623/1.15 |
| 9,381,103 B2 * | 7/2016 | Abunassar | ................ | A61F 2/89 |
| 2004/0153140 A1 * | 8/2004 | Rolando | ................... | A61F 2/91 623/1.16 |

(Continued)

*Primary Examiner* — Alvin Stewart
(74) *Attorney, Agent, or Firm* — Squire Patton Boggs (US) LLP

(57) ABSTRACT

A stent includes a plurality of rings which form a tubular scaffold. The rings include an elongation mechanism which allows for further expansion of the stent.

7 Claims, 12 Drawing Sheets

(56) References Cited

U.S. PATENT DOCUMENTS

| | | | | |
|---|---|---|---|---|
| 2006/0100690 A1* | 5/2006 | Venturelli | A61F 2/856 | 623/1.15 |
| 2007/0043426 A1* | 2/2007 | Abbate | A61F 2/91 | 623/1.15 |
| 2007/0055365 A1* | 3/2007 | Greenberg | A61F 2/01 | 623/1.44 |
| 2007/0067017 A1* | 3/2007 | Trapp | A61F 2/91 | 623/1.16 |
| 2007/0100434 A1* | 5/2007 | Gregorich | A61F 2/91 | 623/1.16 |
| 2008/0071354 A1* | 3/2008 | Das | A61F 2/91 | 623/1.15 |
| 2008/0114441 A1* | 5/2008 | Rust | A61F 2/07 | 623/1.13 |
| 2008/0167706 A1* | 7/2008 | Ley | A61F 2/91 | 623/1.15 |
| 2008/0188924 A1* | 8/2008 | Prabhu | A61F 2/82 | 623/1.16 |
| 2008/0255655 A1* | 10/2008 | Kusleika | A61F 2/91 | 623/1.11 |
| 2008/0319528 A1* | 12/2008 | Yribarren | A61F 2/91 | 623/1.15 |
| 2009/0005858 A1* | 1/2009 | Young | A61F 2/91 | 623/1.34 |
| 2009/0088831 A1* | 4/2009 | Goto | A61F 2/91 | 623/1.11 |
| 2009/0093875 A1* | 4/2009 | Stalker | A61L 31/022 | 623/1.42 |
| 2010/0049304 A1* | 2/2010 | Clifford | A61F 2/91 | 623/1.16 |
| 2010/0063581 A1* | 3/2010 | Pappas | A61F 2/91 | 623/1.15 |
| 2010/0131044 A1* | 5/2010 | Patel | A61F 2/915 | 623/1.16 |
| 2011/0054592 A1* | 3/2011 | Fliedner | A61F 2/856 | 623/1.16 |
| 2011/0202122 A1* | 8/2011 | Takeuchi | A61F 2/91 | 623/1.2 |
| 2012/0016458 A1* | 1/2012 | Abunassar | A61F 2/89 | 623/1.15 |
| 2013/0079865 A1* | 3/2013 | Poehlmann | A61F 2/915 | 623/1.15 |
| 2013/0304192 A1* | 11/2013 | Chanduszko | A61F 2/90 | 623/1.16 |
| 2014/0288635 A1* | 9/2014 | Shalev | A61F 2/07 | 623/1.16 |
| 2016/0256300 A1* | 9/2016 | Abunassar | A61F 2/89 | |

* cited by examiner

STENT WITH ELONGATING STRUTS

This application is a continuation of U.S. patent application Ser. No. 14/507,634 filed Oct. 6, 2014, which is incorporated by reference herein.

FIELD OF THE INVENTION

This invention relates generally to implantable medical devices and, more particularly, to stents.

BACKGROUND

Stents are frequently used in the medical field to open vessels affected by conditions such as stenosis, thrombosis, restenosis, vulnerable plaque, and formation of intimal flaps or torn arterial linings caused by percutaneous transluminal coronary angioplasty (PCTA). Stents are used not only as a mechanical intervention, but also as vehicles for providing biological therapy. As a mechanical intervention, stents act as scaffoldings, functioning to physically hold open and, if desired, to expand a vessel wall. Stents may be capable of being compressed in diameter, so that they can be moved through small vessels with the use of a catheter or balloon-catheter, and then expanded to a larger diameter once they are at the target location. Examples of such stents include those described in U.S. Pat. No. 4,733,665 to Palmaz, U.S. Pat. No. 4,800,882 to Gianturco, U.S. Pat. No. 4,886,062 to Wiktor, U.S. Pat. No. 5,514,154 to Lau et al., and U.S. Pat. No. 5,569,295 to Lam.

A stent must have sufficient radial strength to withstand structural loads, such as radial compressive forces, imposed on the stent as it supports the walls of a vessel or other anatomical lumen. In addition, the stent must possess sufficient flexibility to allow for crimping, deployment, and cyclic loading from surrounding tissue. Also, a sufficiently low profile, that includes diameter and size of struts, is important. As the profile of a stent decreases, the easier is its delivery through an anatomical lumen, and the smaller the disruption in the flow of blood or other bodily fluid.

Metal stents typically stay implanted in a patent for a longer amount of time than bioresrobable polymer stents. For example, metal stents can be implanted for years or permanently in a patient. Since bioresrobable polymer stents degrade over time, they gradually allow for native positive remodeling of the anatomical lumen, which involves allowing the anatomical lumen to enlarge naturally. On the other hand, metal stents can prevent positive remodeling.

Stents made of bioresorbable polymers have been developed to allow for improved healing of the anatomical lumen. Examples of bioresorbable polymer stents include those described in U.S. Pat. No. 8,002,817 to Limon, U.S. Pat. No. 8,303,644 to Lord, and U.S. Pat. No. 8,388,673 to Yang.

Scaffold designs for stents made of bioresorbable polymers involve a balance between radial strength and expansion capability. Bars that are shorter in length generally provide greater radial strength, in that the scaffold can withstand a greater inward radial force without collapsing to a smaller diameter from a fully deployed state, as compared to a scaffold having bars that are longer in length. However, the increase in radial strength provided by shorter bars usually comes at the expense of expansion capability. A scaffold with longer bars provides increased expansion capability, in that the scaffold provides less resistance to being expanded from a fully crimped state to a fully deployed state, as compared to a scaffold with shorter bars. The increase in expansion capability provided by longer bars usually comes at the expense of radial strength.

Accordingly, there is a continuing need for stent strut configurations and manufacturing methods that facilitate delivery of polymer stents with maximized radial strength and expansion capability.

SUMMARY

Briefly and in general terms, the present invention is directed to an implantable stent and a method for making an implantable stent.

In aspects of the invention, a stent comprises a plurality of rings, each ring including an alternating series of bars and hinges, each hinge configured to bend inward to allow the ring to be radially compressed from a manufactured state to a crimped state, each hinge configured to bend outward to allow the ring to radially expand from the crimped state to a deployed state. The stent further comprises a plurality of links connecting the rings together. The rings and links form a tubular scaffold having a central axis. At least one of the bars includes an elongation mechanism having a folded configuration when the ring is in the manufactured state and the crimped state and having unfolded configuration when the ring is in the deployed state.

In aspects of the invention, a method of making a stent comprises forming a plurality of rings, each ring including an alternating series of bars and hinges, each hinge configured to bend inward to allow the ring to be radially compressed from a manufactured state to a crimped state, each hinge configured to bend outward to allow the ring to radially expand from the crimped state to a deployed state. The method further comprises forming a plurality of links connecting the rings together, wherein the rings and links form a tubular scaffold having a central axis. The method further comprises forming within at least one of the bars an elongation mechanism having a folded configuration when the ring is in the manufactured state. The elongation mechanism is configured to remain in the folded configuration when the ring is in the crimped state, and the elongation mechanism configured to unfold to an unfolded configuration when the ring is in the deployed state.

In aspects of the invention, a stent comprises a plurality of rings, each ring including an alternating series of bars and hinges, each hinge configured to bend inward to allow the ring to be radially compressed from a manufactured state to a crimped state, each hinge configured to bend outward to allow the ring to radially expand from the crimped state to a first deployed state and further radially expand a second deployed state. The stent further comprises a plurality of links connecting the rings together. The rings and links form a tubular scaffold having a central axis. At least one of the bars includes a plurality of pivots and fingers having a folded configuration when the ring is in a crimped state, the pivots and fingers are configured to remain in the folded configuration when the ring is radially expanded from the crimped state to the first deployed state, and are configured to unfold from the folded configuration when the ring radially expands from the first deployed state to the second deployed state.

Any one or a combination of two or more of the following can be appended to the above aspects of the invention to form additional aspects of the invention.

The elongation mechanism includes a plurality of cuts, a first cut of the plurality of cuts is formed in a first side surface of a bar, a second cut of the plurality of cuts is formed in a second side surface of the bar, each of the cuts has a cut radial depth that is at least 70% of a bar radial thickness of the bar, and the cut radial depth and the bar radial thickness are in a direction perpendicular to the central axis of the tubular scaffold.

The plurality of cuts includes at least three cuts, and the cuts alternate along a length of the bar such that the first cut formed in the first side surface is immediately followed by the second cut formed in the second side surface, and the second cut is immediately followed by a third cut formed in the first side surface.

Each of the cuts in the bar has a cut transverse depth that is less than a bar transverse width of the bar, the cut transverse depth is from 10% to 70% of the bar transverse width, the cut transverse depth and the bar transverse width are in a direction perpendicular to any of the first side surface and the second side surface.

When the elongation mechanism is viewed from a radially inward direction perpendicular to the central axis, the cuts form an S-shape of material that is compressed when the ring is in the manufactured state and the crimped state, and the S-shape of material is configured to elongate out of the folded state when the ring is placed in the deployed state.

Each cut includes two interior surfaces that contact each other when the ring is in the crimped state, and the two interior surfaces do not contact each other when the ring is in the deployed state.

The deployed state corresponds to a second deployed state such that the two interior surfaces do not contact each other when the ring is in the second deployed state, each hinge is configured to bend outward to allow the ring to radially expand from the crimped state to a first deployed state and then from first deployed state to the second deployed state, and the two interior surfaces contact each other when the ring is in the crimped state and the first deployed state.

The deployed state corresponds to a second deployed state such that the elongation mechanism is in the unfolded configuration when the ring is in the second deployed state, each hinge is configured to bend outward to allow the ring to radially expand from the crimped state to a first deployed state and then from first deployed state to the second deployed state, and the elongation mechanism is in the folded configuration when the ring is in the manufactured state, the crimped state, and the first deployed state.

Each hinge is configured to bend outward to allow the ring to radially expand from the crimped state to the first deployed state such that when the hinge bends outward, bars on each side of the hinge form an interior angle of at least 60 degrees when the ring is in the first deployed state.

At least one of the bars in each of the rings includes an elongation mechanism.

At least two of the bars in the same ring include an elongation mechanism.

The elongation mechanism includes a discontinuous cut formed into the bar, the bar is made of a core material that forms a bridge across the discontinuous cut.

The elongation mechanism includes a cut formed into the bar, and a vasodilator agent is disposed within the cut.

The pivots and fingers are formed by cuts in the side surfaces of the at least one bar.

The bar is made of a core material, and the pivots and fingers form an S-shape of core material.

The core material is a polymer or a metal.

The ring is configured to provide support to an anatomical lumen when the ring is in the first deployed state.

The ring is configured to provide support to an anatomical lumen when the ring is in the first deployed state.

The features and advantages of the invention will be more readily understood from the following detailed description which should be read in conjunction with the accompanying drawings.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION OF EXEMPLARY EMBODIMENTS

As used herein, a stent is a device that is placed inside the body of a person or animal and, more particularly, within an anatomical lumen or cavity. Examples of anatomical lumen and cavities in which a stent can be placed include without limitation arterial or venous vasculature, urethra, ureter, fallopian tubes, esophagus, and the like. Non-limiting examples of stents within the scope of the present invention are those which are self-expanding and balloon expandable, and which are configured for percutaneous transluminal delivery methods. Stents which have a finite lifetime in vivo are sometimes referred to as scaffolds due to their temporary nature.

As used herein, "bioresorbable" refers to a material capable being completely eroded, degraded (either biodegraded and/or chemically degraded), and/or absorbed when exposed to bodily fluids (such as blood or other fluid); and can be gradually resorbed, absorbed and/or eliminated by the body. Other terms such as biodegradable, bioabsorbable, and bioerodible may be found in the literature and while these terms have specific definitions, they are often used interchangeably.

As used herein, "biostable" refers to a material that is not bioresorbable.

As used herein, "abluminal surface" refers to a radially outward facing surface. For example, an abluminal surface of an implanted stent is the surface that faces toward and contacts the walls of a blood vessel or other anatomical lumen.

As used herein, "luminal surface" refers to a radially inward facing surface. For example, a luminal surface of an implanted stent is the surface that faces toward the center of the blood vessel or other anatomical lumen. Blood or other bodily fluids may flow across the luminal surface of an implanted stent.

A used herein, "side surface" refers to a surface which is disposed between and which connects an abluminal surface to a luminal surface.

The word "distal" when used in the context of a device, refers to a portion of the device located at the front of the device or which faces in a forward direction during typical use of the device. The word "proximal" when used in the context of a device, refers to a portion of the device located at the rear of the device or which faces in a rearward direction during typical use of the device.

Figure 1:
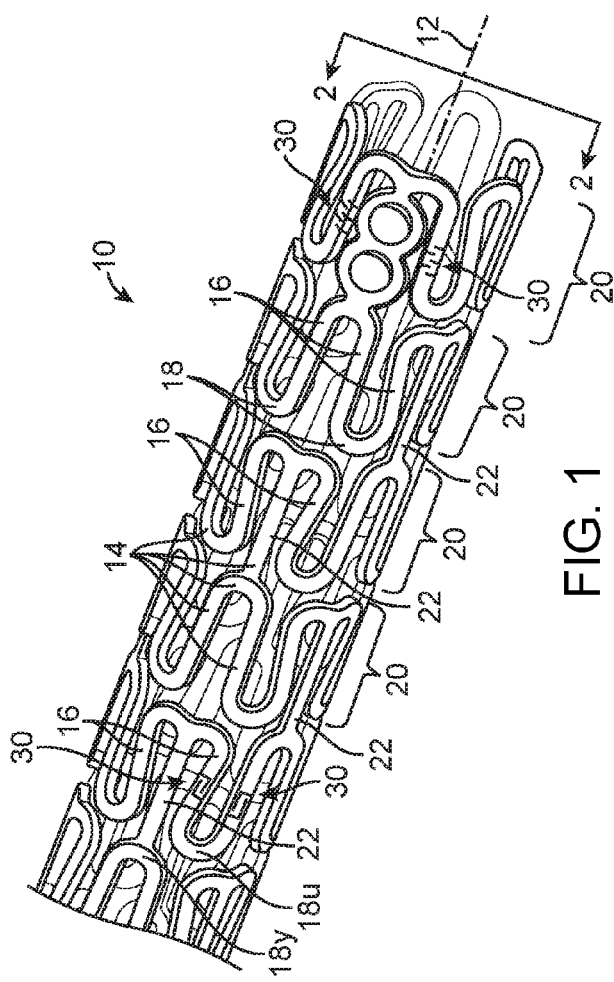
FIG. 1 is a perspective view of a stent.

Referring now in more detail to the exemplary drawings for purposes of illustrating embodiments of the invention, wherein like reference numerals designate corresponding or like elements among the several views, there is shown in FIG. 1 an end segment of exemplary stent 10. Stent 10 can be implanted by itself, in combination with other stents, or as part of implant assembly. For example, stent 10 can be part of a graft device or stent-graft device.

Stent 10 has a cylindrical shape with central axis 12 and includes a pattern of interconnecting structural elements referred to as stent struts 14. Axis 12 extends through the center of the cylindrical shape formed by struts 14. The stresses that arise during compression and deployment are generally distributed throughout various struts 14 but can be concentrated at strut junctions referred to as hinges 18.

Bars 16 are one type of stent strut. Bars 16 are connected to each other by hinges 18. Bars 16 and hinges 18 form rings 20. Rings 20 can change in diameter due to the sinusoidal structural configuration of the rings. Within each ring 20, bars 16 alternate with hinges 18 to form a repeating series as follows: bar, hinge, bar, hinge, and so on. This repeating series forms the sinusoidal pattern of each ring 20. Multiple rings 20 are arranged longitudinally and are centered on axis 12. Links 22 are another type of stent strut. Links 22 connect rings 20 to each other. Rings 20 and links 22 collectively form a tubular scaffold of stent 10.

Referring now to FIGS. 2A-2D, stent 10 can be more easily passed through a blood vessel, urinary tract, or other type of anatomical lumen when stent 10 is radially compressed. Radial compression is accomplished by a crimping process performed prior to passing stent 10 through the anatomical lumen. Radial compression occurs in the direction of arrows 17 (FIG. 2A) perpendicular central axis 12. The crimping process can be performed while stent 10 is disposed around catheter 24 so that radial compression of stent 10 secures stent 10 to catheter 24. Catheter 24 can then be used to pass stent 10 through the anatomical lumen. Various devices for crimping, such as a sliding wedge crimper, are known and need not be described herein.

After stent 10 is passed through the anatomical lumen, stent 10 is deployed at the desired region of the anatomical lumen. Deployment is the process of radial expansion of stent 10 within the anatomical lumen. Radial expansion occurs in the direction of arrows 21 (FIG. 2B) perpendicular central axis 12. Deployment can be accomplished by inflating a balloon portion of catheter 24 on which stent 10 is mounted. Additionally or alternatively, deployment can also occur as a result of self-expansion of stent 10 after removal of a constrictive sheath that optionally surrounds stent 10 while the stent is being passed through the anatomical lumen.

After deployment, stent 10 is subjected to static and cyclic compressive loads from surrounding tissue of the anatomical lumen. Rings 20 are configured to maintain the radially expanded state of stent 10 after deployment.

Stent 10 can be manufactured by forming a thin-walled tube by one or more processes, such as extrusion, blow molding, injection molding, and other process. For example, a flat sheet of material can be rolled to form a thin-walled tube. The thin-walled tube can be made from one or more bioresorbable polymers, one or more biostable polymers, or combinations thereof. The thin-walled tube is also referred to as a precursor tube since it is the structure used to make the tubular scaffold of the stent. The core of each bar 16, hinge 18, and link 22 will be made of the polymer material of the thin-walled tube.

Figure 2D:
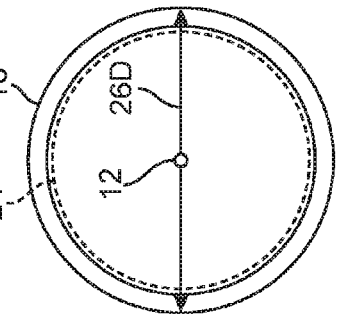
FIGS. 2C and 2D are end views of the stent in the direction of lines 2-2 of FIG. 1 and show the stent in deployed states.

Portions of the precursor tube are removed so that what remains of the precursor tube is the tubular scaffold in the form of rings 20 interconnected by links 22. Removal of material from the precursor tube can be accomplished by a laser, mechanical cutter, chemical etching, and/or other processes. The manufactured state of the tubular scaffold is the structural configuration that is present after removal of material from the precursor tube and before any crimping. Alternatively, the tubular scaffold can be formed using a mold or die (such as by casting, extrusion, injection molding, and/or blow molding), and the manufactured state is the structural configuration that is present after the tubular scaffold is separated from the mold or die and before any crimping. FIGS. 2A, 3A, 4A, 5, 6, 9A-9C, 11, and 13A-13C show parts of tubular scaffolds in manufactured states. When in the crimped state, stent 10 (specifically the tubular scaffold, and more specifically each ring 20) has outer diameter 26A (FIG. 2A).

The tubular scaffold of stent 10 is radially compressed by a crimping process, which changes the tubular scaffold from a manufactured state to a crimped state. FIGS. 1, 2B, 3B, and 4B show tubular scaffolds in crimped states. When in the crimped state, stent 10 (specifically the tubular scaffold, and more specifically each ring 20) has outer diameter 26B (FIG. 2B) which is less than diameter 26A.

When stent 10 is at the desired location within the anatomical lumen of a patient, the tubular scaffold of stent 10 is radially expanded (or allowed to self-expand) from its crimped state to a deployed state. When in a deployed state, stent 10 (specifically the tubular scaffold, and more specifically each ring 20) has an outer diameter that is greater than diameter 26B of the crimped stated. The outer diameter of the deployed stent can be less than, equal to, or greater than diameter 26A.

Figure 2C:
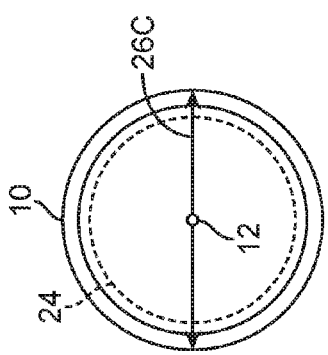
Figure 3A:
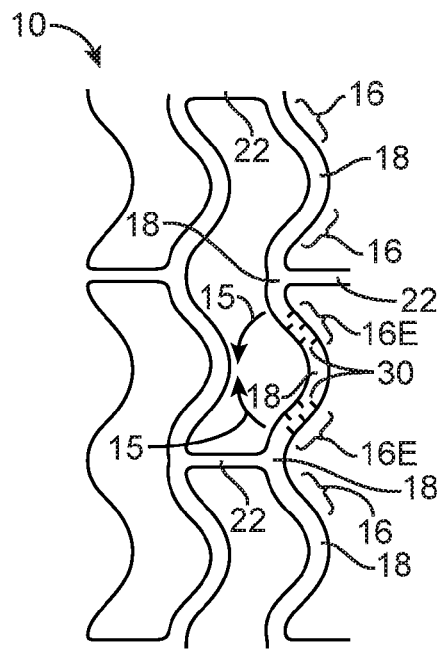
FIGS. 3A-3D are a chronological sequence of views of the stent, the views showing an elongation mechanism at a manufactured state, at a crimped state, at completion of a first phase of deployment, and at completion of a second phase of deployment.
Figure 3B:
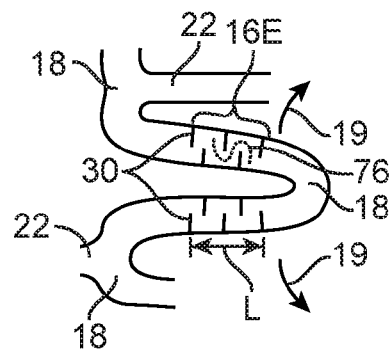
Figure 3C:
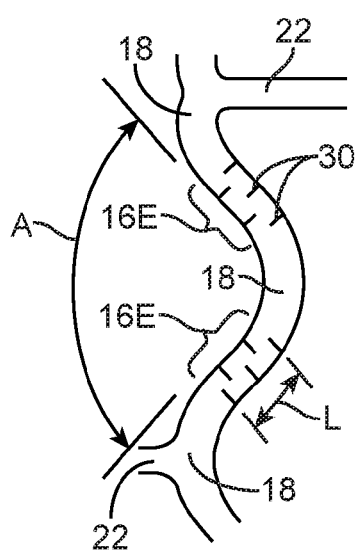
Figure 3D:
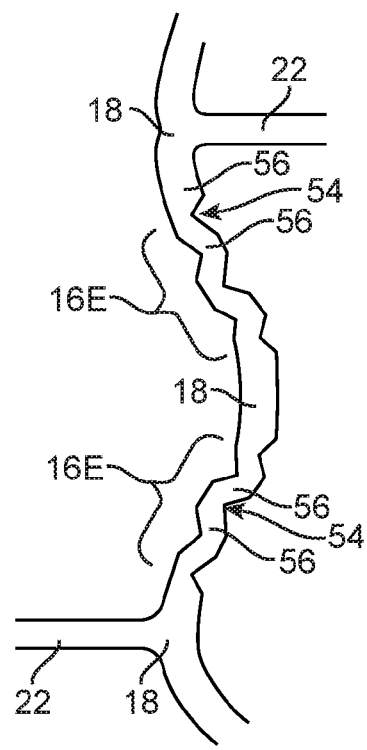
Figure 4A:
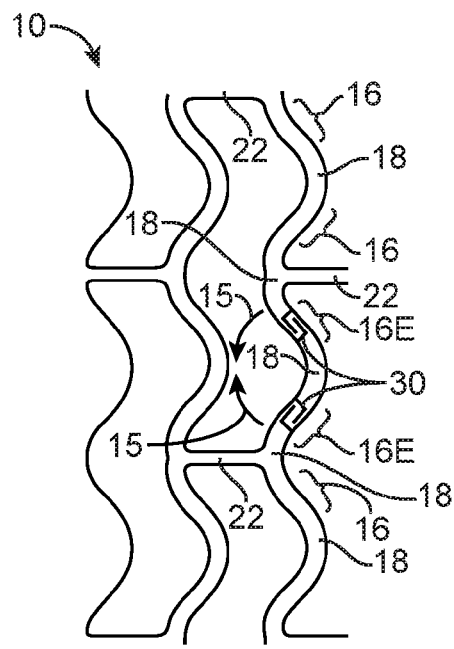
FIGS. 4A-4D are a chronological sequence of views of the stent, the views showing another elongation mechanism at a manufactured state, at a crimped state, at completion of a first phase of deployment, and at completion of a second phase of deployment.
Figure 4B:
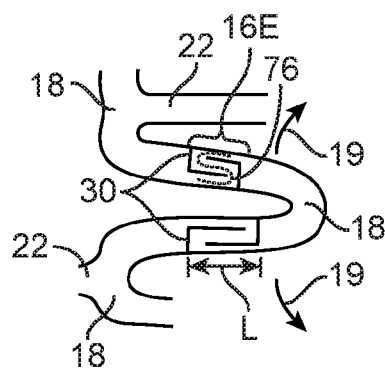
Figure 4C:
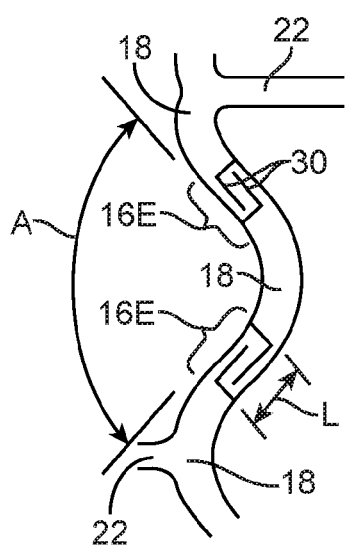
Figure 4D:
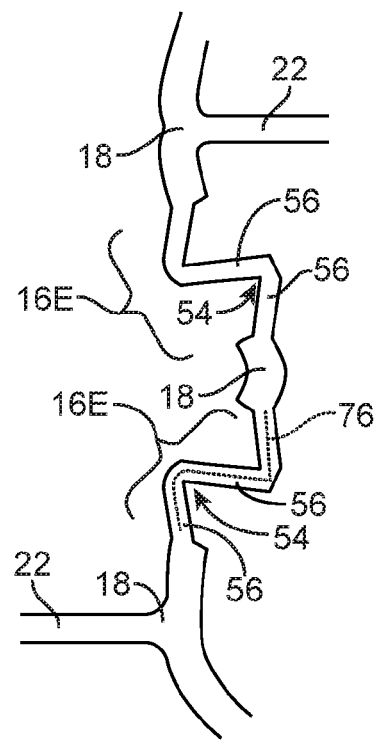

FIGS. 2C, 3C, and 4C show tubular scaffolds in a first deployed state, which corresponds to completion of a first phase of deployment which will be described below. In some aspects, tubular scaffolds (including rings with elongation mechanisms described below) are capable of supporting an anatomical lumen, such that the anatomical lumen is held open, when the tubular scaffold is in the first deployed state. FIGS. 2D, 3D, and 4D show tubular scaffolds in a second deployed state, which corresponds to completion of a second phase of deployment which will be described below. In some aspects, tubular scaffolds (including rings with elongation mechanisms described below) are capable of supporting an anatomical lumen, such that the anatomical lumen is held open, when the tubular scaffold is in the second deployed state.

Figure 2B:
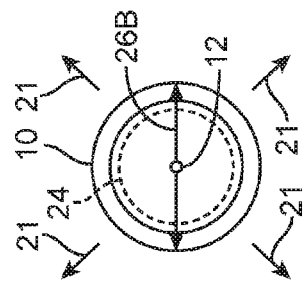
FIGS. 2A and 2B are end views of the stent in the direction of lines 2-2 of FIG. 1 and show an outer diameter of the stent while in a manufactured state and a crimped state, respectively.
Figure 2A:
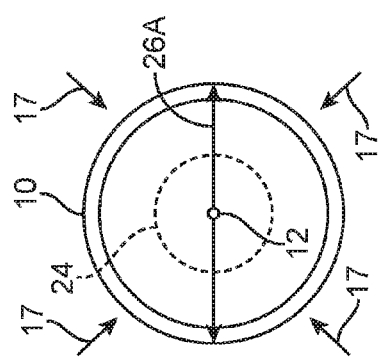

As previously mentioned, FIG. 2A shows stent 10 before any crimping is performed and at which time the tubular scaffold has outer diameter 26A. Diameter 26A can be the outer diameter of the precursor tube before it is cut in order to form the tubular scaffold. Diameter 26A can be the outer diameter of the precursor tube after it is cut but before any crimping. FIG. 2B shows stent 10 at completion of crimping, at which time the tubular scaffold has diameter 26B which is less than diameter 26A. Diameter 26A can be at least 20%, at least 40%, or at least 60% greater than diameter 26B.

FIG. 2C shows stent 10 at completion of a first phase of deployment, at which time the tubular scaffold has diameter 26C. FIG. 2D shows stent 10 at completion of a second phase of deployment, at which time the tubular scaffold has diameter 26D which is substantially greater than diameter 26C. Here, "substantially greater" means at least 2% greater than diameter 26C. For example, diameter 26D can be at least 5%, or at least 10%, or at least 20% greater than diameter 26C.

Typically, bars 16 would be manufactured to have a greater length in order to allow stent 10 to expand to a greater diameter. However, increasing the length of bars 16 is associated with a decrease in radial strength of the stent 10. A decrease in radial strength would make stent 10 less able to withstand static and cyclic compressive loads from surrounding tissue of the anatomical lumen.

Embedded within at least some bars 16 are elongation mechanisms 30 that can allow stent 10 to expand to a greater diameter without having to increase the length of bars 16 and thus avoid a decrease in the radial strength of stent 10.

In the description below, bars that have an elongation mechanism are called "elongating bars." Bars that do not have an elongation mechanism called "non-elongating bars." Unless indicated otherwise, reference numeral 16 refers to bars with and without an elongation mechanism. Reference numeral 16E refers only to bars with an elongation mechanism (i.e., refers only to elongating bars).

FIGS. 3A-3D and 4A-4D show elongating bars 16E at exemplary portions of rings 20 of stent 10. FIGS. 3A-3D show a first embodiment of elongation mechanism 30. FIGS. 4A-4D show a second embodiment of elongation mechanism 30.

FIGS. 3A and 4A show elongating bars 16E of tubular scaffolds in manufactured states. FIGS. 3B and 4B show elongating bars 16E of tubular scaffolds in crimped states. During stent crimping, hinges 18 bend inward in the direction of arrows 15 (FIGS. 3A and 4A) to allow bars 16 to move closer to each other. Stent 10 (specifically the tubular scaffold, and more specifically each ring 20) radially compresses as bars 16 move closer together. Radial compression occurs in the direction of arrows 17 (FIG. 2A) perpendicular central axis 12.

In some embodiments, elongating bars 16E do not change in length during crimping, or more specifically, do not shorten in length during crimping. In alternative embodiments, elongating bars 16E shorten in length by no more than 5% from the start of crimping to the end of crimping. The length, L, of the elongating bar is its end-to-end dimension measured from opposite ends attached to hinges 18.

FIGS. 3C and 4C show elongating bars 16E of tubular scaffolds at completion of a first phase of deployment, at which time rings 20 have diameter 26C that allows rings 20 to make contact with and provide support to the walls of the anatomical lumen.

During the first phase of deployment, hinges 18 bend outward in the direction of arrows 19 (FIGS. 3B and 4B) to allow bars 16 to move apart from each other. Stent 10 (specifically the tubular scaffold, and more specifically each ring 20) radially expands as bars 16 move apart. Radial expansion occurs in the direction of arrows 21 (FIG. 2B) perpendicular central axis 12.

The first phase of deployment proceeds as follows. Hinges 18 bend outward to allow adjacent bars 16 to move apart from each other and thereby allow the tubular scaffold to go from the crimped state to the deployed state. Hinges 18 bend outward to at least a minimum angle, A, that is at least 45 degrees, at least 60 degrees, at least 90 degrees, or at least 110 degrees. The angle, A, is defined as the interior angle between a pair of bars 16 connected by one of the hinges. During the first phase of deployment and before hinges 18 reach the minimum angle, the elongating bars 16E do not change in length, or more specifically, do not increase in length. Alternatively, during the first phase and before hinges 18 reach the minimum angle, the elongating bars 16E increase in length by no more than 5%.

A second phase of expansion provides potential safety benefits when the user, an interventional cardiologist or radiologist typically, over-expands a scaffold beyond the intended final lumen size. A degree of over-expansion may be specifically be required when stenting an aggressive stenosis or total occlusion blockage. In these cases, a second phase of expansion (over-expansion beyond the first phase) may be required to crack or deform a plaque in order to reduce the degree of stent recoil and chronic force exerted on the stent outer surface.

Another reason a degree of stent over-expansion is useful is in the treatment of long blockages in tapered vessels. Typically, proximal artery segments are larger in diameter when compared to more distal artery segments. When treating long lesions with long stents (38 or 48 mm coronary stents have been commercialized), a single tubular stent size may lack the effective range of deployment to appose to the vessel wall at both the proximal and distal edges of the stent. In these cases, conventional stents would be designed with excessively long bar arm segments to accommodate a full range of potential deployment, however, this design philosophy (of making bar arm longer) results in sub-optimal radial strength.

A second phase of expansion could also be useful when deploying stents or stent grafts in young patients. In these cases, a vessel lumen will naturally grow over years after stent implantation. An implant that accommodates natural growth potential is desirable in these cases, either by naturally expanding to an enlarging state over time or with touch-up balloon inflation procedures. Other cases of natural vessel growth can be attributed to changes in exercise behavior or changes in patient heart mass over time. These vessel size changes may not be accommodated by conventional balloon expandable stents.

FIGS. 3D and 4D show elongating bars 16E of tubular scaffolds at completion of a second phase of deployment. Elongation mechanism 30 facilitates further expansion of the tubular scaffold during the second phase of deployment. The second phase begins after completion of the first phase, which is when hinges 18 have reached the minimum angle, A, described above. During the second phase of deployment, hinges 18 do not bend outward, or hinges 18 may continue to bend outward but with greater resistance to bending as compared to the first phase of deployment. During the second phase, tension in the bars 16 increases due to inability or a decrease in the ability of hinges 18 to bend outward. The tension pulls ends of bars 16 in opposite directions. To relieve the tension, elongating bars 16E increase in length by at least 5%, at least 10%, or at least 20% from the start of the second phase. The increase in length of elongating bars 16E is greater than an increase in length, if any, of non-elongating bars 16. In some embodiments, non-elongating bars 16 increase in length by no more than 2% (possibly due to deformation) during the second phase.

The first phase of deployment can be achieved by inflating a balloon portion of catheter 24 on which stent 10 is mounted. Inflation of the balloon causes the tubular scaffold to increase in size from diameter 26B to diameter 26C. At diameter 26C, stent 10 contacts and supports the walls of the anatomical lumen. Afterwards, the balloon portion can be inflated further. This can be referred to as over-inflation. Over-inflation results in the second phase of deployment, during which the tubular scaffold increases in size from diameter 26C to diameter 26D. This additional increase to diameter 26D occurs due to unfolding of one or more elongation mechanisms 30.

After completion of the second phase of deployment, the balloon portion of catheter 24 is deflated and catheter 24 can be removed from the anatomical lumen while stent 10 remains in place within the anatomical lumen. When the balloon portion is deflated, the tubular scaffold reduces in size from diameter 26D to diameter 26C. This reduction in size occurs due to collapse of one or more elongation mechanisms 30. Stent 10 is able to maintain diameter 26C and avoid further reduction in diameter because collapse of each elongation mechanism 30 is limited by the structural configuration of elongation mechanism. Cut interior surfaces (discussed below) of elongation mechanism 30 can make contact and press against each other when stent 10 reaches diameter 26C so that further reduction below diameter 26C is prevented or inhibited. A further reduction in size below diameter 26C is referred to as "recoil" and is undesirable since such a reduction may result in less mechanical support for the anatomical lumen.

Figure 5:
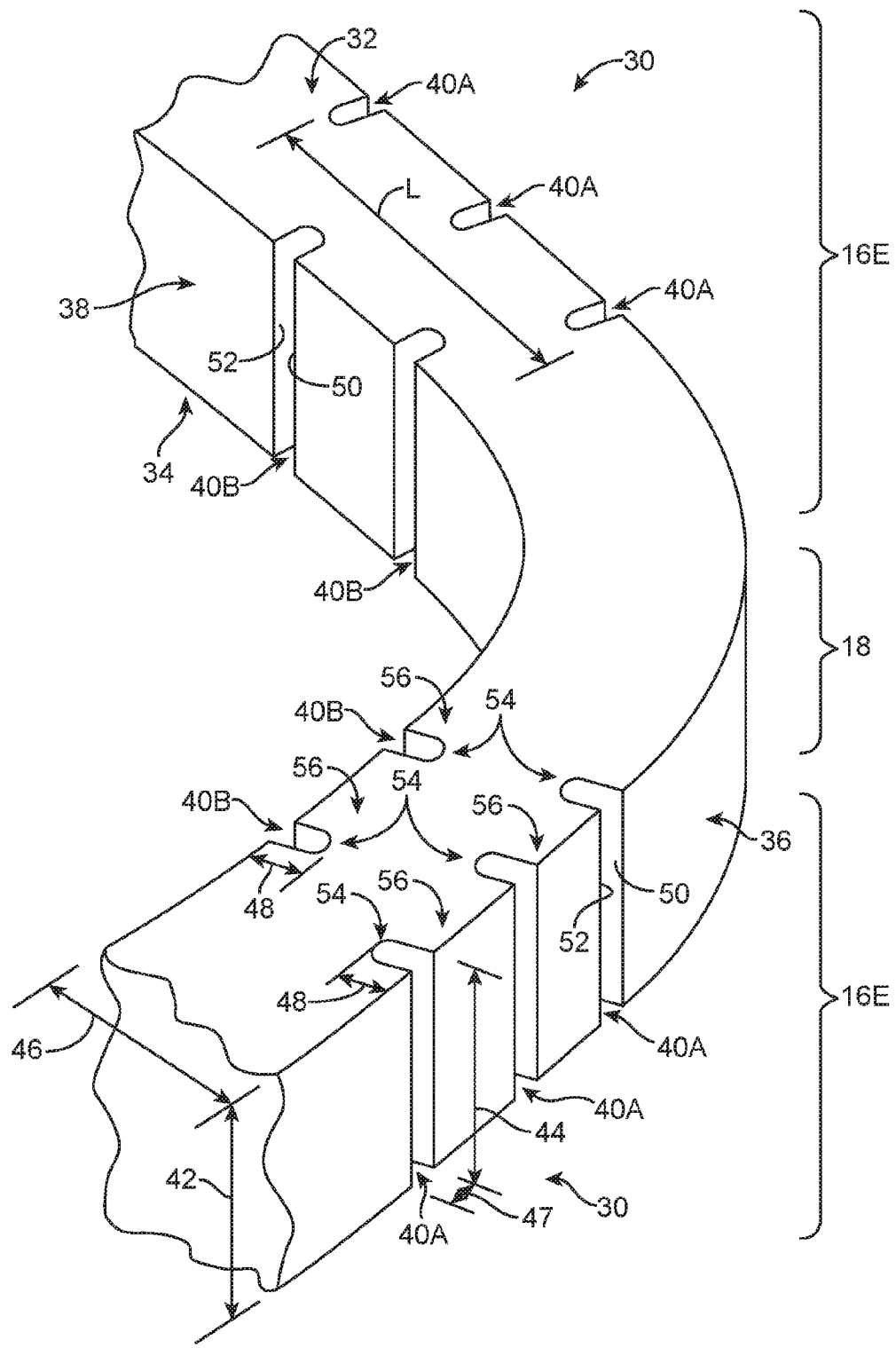
FIG. 5 is a perspective view showing the elongation mechanism of FIG. 3A.

FIG. 5 shows an enlarged view of elongation mechanism 30 of FIG. 3A. Stent 10 (specifically the tubular scaffold, and more specifically each elongating bar 16E) includes abluminal surface 32, luminal surface 34, first side surface 36, and second side surface 38. First side surface 36 and second side surface 38 are at opposite sides of elongating bar 16E. Elongation mechanism 30 includes a series of cuts 40 formed into first and second side surfaces 36, 38 of elongating bar 16E. There are no cuts 40 present at first and second side surfaces 36, 38 of hinge 18.

Cuts 40 can be formed by cutting the precursor tube while also cutting rings 20 and links 22 to form the tubular scaffold. The same laser or mechanical knife can be used to make cuts 40, rings 20, and links 22. Alternatively, cuts 40 can be formed after the tubular scaffold is made. For example, the tubular scaffold can be made be made by injection molding, and cuts can be made in a subsequent process using a laser or mechanical knife.

In FIG. 5, each cut 40 extends entirely through radial thickness 42 of elongating bar 16E. Each cut 40 has cut radial depth 44 that is 100% of bar radial thickness 42 at the cut when the tubular scaffold is in the manufactured state. Bar radial thickness 42 and cut radial depth 44 are measured in a direction perpendicular to central axis 12 (FIG. 1) of the tubular scaffold.

In FIG. 5, each cut 40 extends entirely through bar radial thickness 42 but does not extend entirely through transverse width 46 of elongating bar 16E. Bar transverse width 46 is the distance between first and second side surfaces 36, 38. Each cut 40 has cut transverse depth 48 that is less than bar transverse width 46. Bar transverse width 46 and cut transverse depth 48 are measured in a direction perpendicular to any of first side surface 36 and second side surface 38.

Cut transverse depth 48 can be from 10% to 70%, or from 10% to 50%, or from 20% to 40% of bar transverse width 46. Also, cut transverse depth can be at least 25% of bar transverse width 46, or can be less than 50% of bar transverse width 46, or can be from 25% to 50% of bar transverse width 46.

Cuts 40 include cuts 40A and cuts 40B. Reference numeral 40 refers to both cuts 40A and cuts 40B unless indicated otherwise. Cuts 40A intersect first side surface 36 but do not intersect second side surface 38. Cuts 40B intersect second side surface 38 but do not intersect first side surface 36. For each elongation mechanism 30, cuts 40A and 40B alternate along the length of elongating bar 16E. This means that, along the length of elongating bar 16E, cut 40A is immediately followed by cut 40B. Elongation mechanism 30 is illustrated with a total of five cuts 40. The total number of cuts 40 can be at least two, at least three, at least four, at least five, or at least six, depending on the amount of length elongation desired during the second phase of deployment. The length, L, of elongating bar 16E is the greatest straight line distance from the first cut to the last cut on elongating bar 16E.

The alternating arrangement of cuts 40A and 40B forms pivots 54 and fingers 56 which are in a folded configuration when the tubular scaffold is in the manufactured and crimped states, as shown in FIGS. 3A and 3B. Each pivot 54 is surrounding by two fingers 56. There is one finger 56 on each side of pivot 54. During the first phase of stent deployment (during deployment starting from FIG. 3B and completing at FIG. 3C), pivots 54 and fingers 56 do not unfold or they unfold only slightly. When pivots 54 and fingers 56 unfold slightly during the first phase, an increase in length, L, of elongating bar 16E is no more than 5%. Subsequently, pivots 54 and fingers 56 unfold during the second phase of stent deployment (during deployment starting from FIG. 3C and completing at FIG. 3D). Unfolding occurs without facture across the entire bar transverse width 46. Unfolding allows an increase in length, L, of elongating bar 16E by at least 5%, at least 10%, or at least 20% from the start of the second phase.

Figure 6:
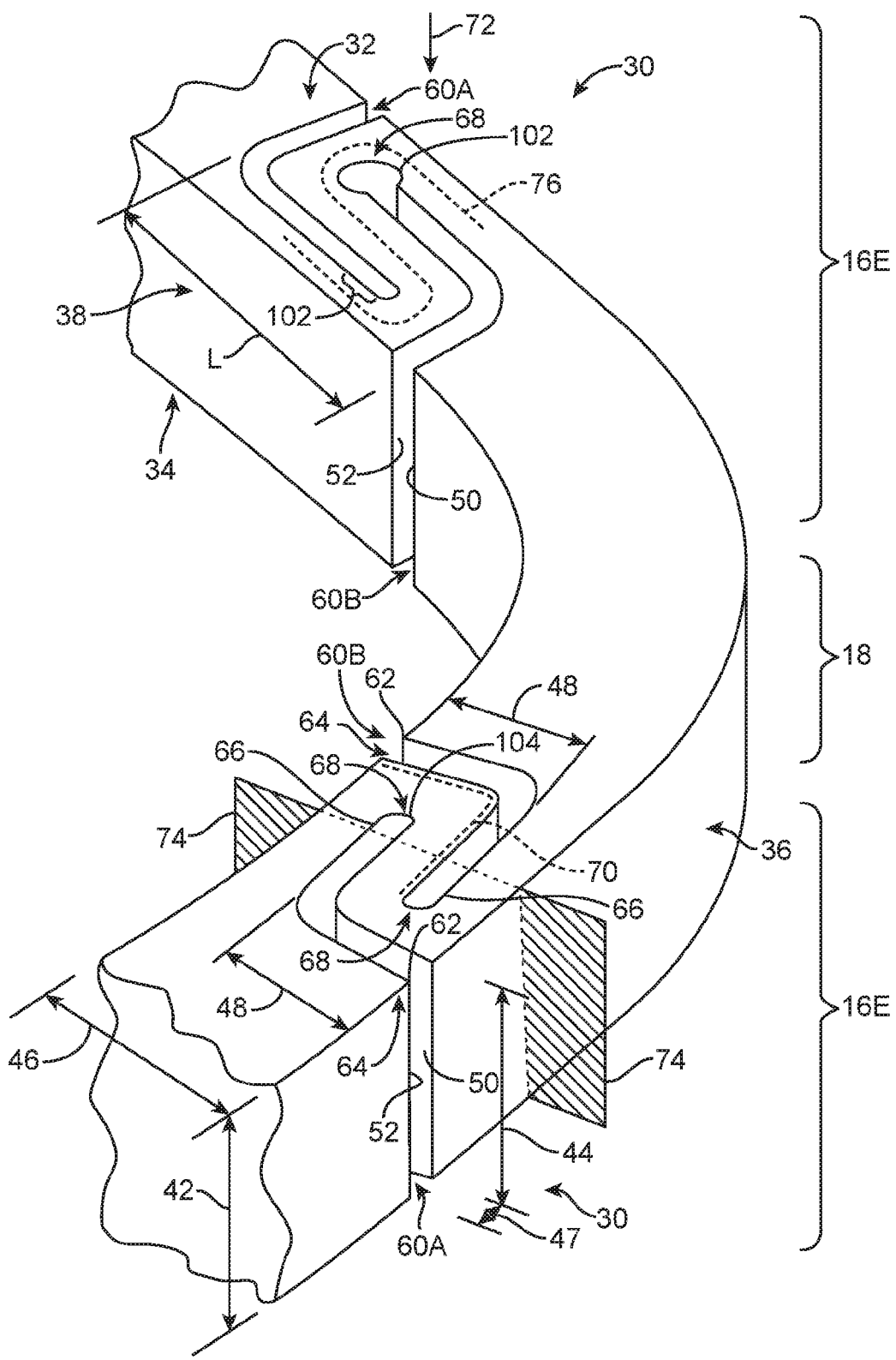
FIG. 6 is a perspective view showing the elongation mechanism of FIG. 4A.

FIG. 6 shows an enlarged view of elongation mechanism 30 of FIG. 4A. Stent 10 (specifically the tubular scaffold, and more specifically each elongating bar 16E) includes abluminal surface 32, luminal surface 34, first side surface 36, and second side surface 38. First side surface 36 and second side surface 38 are at opposite sides of elongating bar 16E. Elongation mechanism 30 includes a series of cuts 60 formed into first and second side surfaces 36, 38 of elongating bar 16E. There are no cuts 60 present at first and second side surfaces 36, 38 of hinge 18.

Cuts 60 can be formed by cutting the precursor tube while also cutting rings 20 and links 22 to form the tubular scaffold. The same laser or mechanical knife can be used to make cuts 60, rings 20, and links 22. Alternatively, cuts 60 can be formed after the tubular scaffold is made. For example, the tubular scaffold can be made be made by injection molding, and cuts can be made in a subsequent process using a laser or mechanical knife.

In FIG. 6, each cut 60 extends entirely through radial thickness 42 of elongating bar 16E. Each cut 60 has cut radial depth 44 that is 100% of bar radial thickness 42 at the cut when the tubular scaffold is in the manufactured state. Bar radial thickness 42 and cut radial depth 44 are measured in a direction perpendicular to central axis 12 (FIG. 1) of the tubular scaffold.

In FIG. 6, each cut 60 extends entirely through bar radial thickness 42 but does not extend entirely through transverse width 46 of elongating bar 16E. Each cut 60 has cut transverse depth 48 that is less than bar transverse width 46. Cut transverse depth 48 can be from 10% to 70%, or from 10% to 50%, or from 20% to 40% of bar transverse width 46. Bar transverse width 46 and cut transverse depth 48 are measured in a direction perpendicular to any of first side surface 36 and second side surface 38. Furthermore, cut transverse depth 48 is measured from point 62 at starting end 64 of cut 60A (or cut 60B) at first side surface 36 (or second side surface 38 for cut 60B) to point 66 furthest away from first side surface 36 (or second side surface 38 for cut 60B).

Opposite ends of each cut 60 are referred to as starting end 64 and terminal end 68. Starting end 64 is located at either first side surface 36 or second side surface 38. Terminal end 68 is not located at any of first and second side surfaces 36, 38. Terminal end 68 is located at an interior region of elongating bar 16E between first side surface 36 and second side surface 38.

Each cut 60 has total length 70 at abluminal surface 32 (or luminal surface 34) from starting end 64 to terminal end 68. Optionally, total length 70 is greater than transverse width 46 of elongating bar 16E. In some embodiments, total length 70 is at least 110%, at least 150%, or at least 200% of transverse width 46.

Cuts 60 include cuts 60A and cuts 60B. Reference numeral 60 refers to both cuts 60A and cuts 60B unless indicated otherwise. Cuts 60A intersect first side surface 36 but do not intersect second side surface 38. Cuts 60B intersect second side surface 38 but do not intersect first side surface 36. For each elongation mechanism 30, cuts 60A and 60B are arranged relative to each other so that they form an S-shape of polymer material when viewed from radially inward direction 72 (FIG. 6). Radially inward direction 72 is perpendicular to central axis 12 (FIG. 1). The S-shape may arise when imaginary transverse plane 74 intersects cut 60A and 60B. Transverse plane 74 is perpendicular to any of first side surface 36 and second side surface 38.

In FIG. 6, elongating bar 16E has one pair of cuts consisting of cut 60A and cut 60B. Each pair of cuts forms the S-shape described above. In alternative embodiments, elongating bar 16E can have more than one pair of cuts, each of which forms the S-shape described above. The total number of pairs of cuts can depend on the amount of elongation desired during the second phase of deployment.

For cuts 60A, starting end 64 is further away from hinge 18 than terminal end 68. For cuts 60B, starting end 64 is closer to hinge 18 than terminal end 68. This is the arrangement shown in FIG. 6. However, the arrangement of cuts 60A and 60B can be reversed as follows: for cut 60B, starting end 64 is further away from hinge 18 than terminal end 68; and for cut 60A, starting end 64 is closer to hinge 18 than terminal end 68.

FIGS. 4A-4D are views of the tubular scaffold in radially inward direction 72 (FIG. 6), and S-shape 76 is labeled in FIGS. 4B, 4D, and 6 as examples. S-shape 76 is compressed when the tubular scaffold is in the manufactured and crimped states. S-shape 76 elongates during deployment, as shown in FIG. 4D. Cuts 60A and 60B forms pivots 54 and fingers 56 which are in a folded configuration when the tubular scaffold is in the manufactured and crimped states. Pivots 54 are located at terminal end 68 (FIG. 6) of each cut. Each pivot 54 is surrounding by two fingers 56. There is one finger 56 on each side of pivot 54.

During the first phase of stent deployment (during deployment starting from FIG. 4B and completing at FIG. 4C), pivots 54 and fingers 56 do not unfold or they unfold only slightly. When pivots 54 and fingers 56 unfold slightly during the first phase of deployment, an increase in length, L, of elongating bar 16E is no more than 5%. Subsequently, pivots 54 and fingers 56 unfold during the second phase of stent deployment (during deployment starting from FIG. 4C and completing at FIG. 4D). Unfolding occurs without facture across the entire bar transverse width 46. Unfolding allows an increase in length, L, of elongating bar 16E by at least 5%, at least 10%, or at least 20% from the start of the second phase.

In FIGS. 5 and 6, each cut 40, 60 has interior surfaces 50, 52 that are parallel to each other. Cut interior surfaces 50, 52 extend from abluminal surface 32 to luminal surface 34. Cut interior surfaces 50, 52 intersect either first side surface 36 or second side surface 38. In some embodiments, interior surfaces 50, 52 do not contact each other when the tubular scaffold is in the manufactured and crimped states. In alternative embodiments, interior surfaces 50, 52 do not contact each other when the tubular scaffold is in the manufactured state and then contact each other in the crimped state. In alternative embodiments, interior surfaces 50, 52 contact each other when the tubular scaffold is in the manufactured and crimped states.

As mentioned above, cut interior surfaces 50, 52 do not contact each other during the manufactured state and/or crimped state. When cut interior surfaces 50, 52 are not in contact, separation distance 47 between cut surfaces can be less than 1% of bar transverse width 46. Alternatively, separation distance 47 can be from 1% to 2% of bar transverse width 46, or from 1% to 2% of bar transverse width 46 at the cut.

In FIGS. 5 and 6, bar transverse width 46 is uniform throughout length, L, of each elongating bar 16E. The length, L, of elongating bar 16E is the greatest straight line distance from the first cut to the last cut on elongating bar 16E. Having a uniform bar transverse width means that bar transverse width 46 is the same throughout length L.

In alternative embodiments, bar transverse width 46 is not uniform throughout length, L, of elongating bar 16E.

In FIGS. 5 and 6, cuts 40, 60 extend entirely through bar radial thickness 42. In alternative embodiments, cut radial depth 44 is less than 100% of bar radial thickness 42 in the manufactured state to help keep elongation mechanism 30 stable during crimping and optionally during the first phase of deployment. For example cut radial depth 44 can be from 70% to 99%, or from 90% to 99%, or from 95% to 99% of bar radial thickness 42 in the manufactured and crimped states, and then cut radial depth 44 propagates to 100% of bar radial thickness 42 during deployment.

As mentioned above, stent 10 can be made of a polymer material so that the core of each bar 16, hinge 18, and link 22 will be made of the polymer material. This polymer material is called the "core polymer material." A process can be performed by providing a precursor tube made of the core polymer material, and then removing sections of the precursor tube so that what remains are the bars, hinges, and links of the tubular scaffold. The core polymer material can be a biostable polymer or a bioresorbable polymer. In any one or more embodiments herein, the bioresorbable polymer material is a material selected from the group consisting of poly(L-lactide) ("PLLA"), poly(L-lactide-co-glycolide) ("PLGA"), poly(D,L-lactide-co-glycolide), poly(L-lactide-co-caprolactone), poly(glycolide-co-caprolactone) and poly(L-lactide-co-D-lactide) ("PLLA-co-PDLA"). Examples of core polymer materials include without limitation the polymers described in U.S. Pat. No. 8,002,817.

Figure 7:
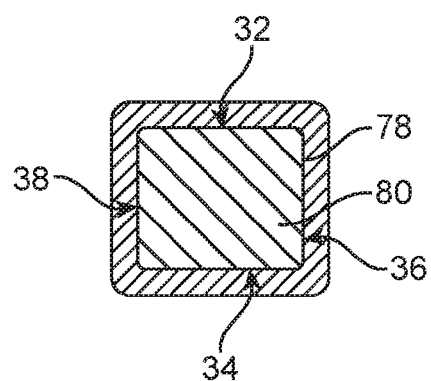
FIG. 7 is a sectional view of a portion of a tubular scaffold.
Figure 8:
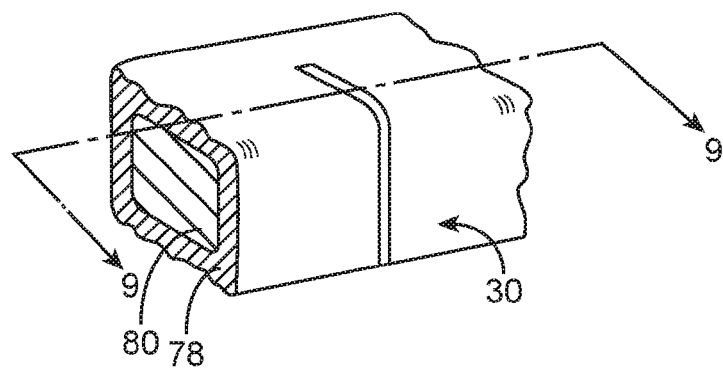
FIG. 8 is a perspective section view of a portion of a tubular scaffold having an elongation mechanism.

As shown in FIGS. 7 and 8, surface coating 78 containing a therapeutic agent, a polymer, a solvent, or a combination thereof, can be applied on core polymer material 80. Core polymer material 80 serves as the substrate for surface coating 78. The coating process can be performed by spraying, immersion, roll coating, or other methods. Therapeutic agents include without limitation drugs and substances that, when administered in therapeutically effective amounts, have a therapeutic beneficial effect on the health and well-being of the patient or subject. Therapeutic agents include without limitation an anti-proliferative, anti-inflammatory or immune modulating, anti-migratory, anti-thrombotic or other pro-healing agent or a combination of two or more thereof. Therapeutic agents include without limitation those described in U.S. Publication Nos. 2010/0244305. Polymers for the coating include without limitation those described in U.S. Pat. No. 8,002,817.

Figures 9A, 9B, 9C:
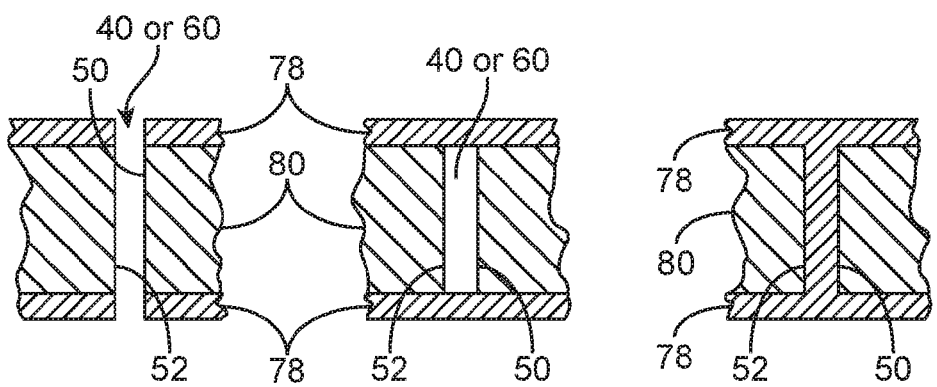
FIGS. 9A-9C are section views along line 9-9 in FIG. 8, showing a cut of the elongation mechanism of FIG. 8.

As mentioned above, stent 10 can be manufactured by removing sections of a precursor tube so that what remains are the bars 16, hinges 18, and links 22 that define the tubular scaffold of stent 10. The surface coating can then be applied to the tubular scaffold. Next, bars 16 can be cut in the manner previously described to form the elongation mechanisms 30. An exemplary result of this cutting process is shown in FIG. 9A. The cutting process will also cut surface coating 78, which can prevent the formation of bridges or webs of coating material across cuts 40, 60. Also, there would be no surface coating present on cut interior surfaces 50, 52. Delamination or peeling of surface coating 78 at elongation mechanisms 30 can be prevented or minimized when cut interior surfaces 50, 52 of each elongation mechanism 30 move apart from each other during deployment.

Alternatively, bars can be cut to form the elongation mechanisms 30 before surface coating 78 is applied to the bars. After the cutting process for the elongation mechanisms 30 is completed, surface coating 78 can be applied to the tubular scaffold. As shown in FIG. 9B, the coating process can be performed so that surface coating 78 covers cuts 40, 60. As shown in FIG. 9C, the coating process can be performed so that surface coating 78 is present on cut interior surfaces 50, 52.

In other embodiments, the coating process (when performed after the cutting process for making elongation mechanisms 30) is performed to selectively avoid application of coating material over cuts 40, 60 to prevent or minimize formation of bridges or webs of coating material across cuts 40, 60. An exemplary result of selective avoidance of cuts 40, 60 is shown in FIG. 9A. Selective avoidance of cuts 40, 60 can be performed as described in U.S. Pat. Nos. 6,395,326 and 7,208,190. By selectively avoiding application of coating material over cuts 40, 60, delamination or peeling of surface coating 78 at elongation mechanisms 30 can be prevented or minimized when cut interior surfaces 50, 52 move apart during deployment.

Figure 10:
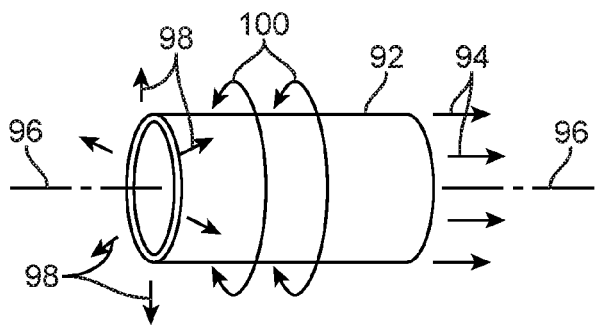
FIG. 10 is perspective view of a precursor tube for making a stent.

Referring to FIG. 10, precursor tube 92 can be used to make the tubular scaffold of stent 10 as previously mentioned. Precursor tube 92 can be made by extruding molten polymer through a die, by rolling a flat sheet of material, or by injection molding. These processes may induce polymer molecule chains to have a preferential orientation. The direction of preferential orientation depends upon the process used to make precursor tube 92. Preferential orientation could be determined by various methods, such as by polarized light microscopy and by x-ray scattering techniques.

An extrusion process may induce polymer molecule chains to have a preferential orientation that is in the direction of extrusion which corresponds to axial directions 94. The extruded tube can also be stretched as part of the extrusion process or as a secondary process after extrusion, as described in U.S. Pat. Nos. 8,192,678 and 7,829,008. Stretching results in stress which causes polymer molecule chains to have a preferential orientation in the direction of stretching. Such stretching can be performed while the core polymer material is at or above its glass transition temperature. For example, precursor tube 92 can be heated to its glass transition temperature and then stretched in axial directions 94 parallel to central axis 96 of precursor tube 92. Central axis 94 of precursor tube 92 eventually becomes central axis 12 of stent 10. Stretching in axial directions 94, such by pulling ends of precursor tube 92 in opposite directions, induces polymer molecule chains to have a preferential orientation in axial directions 94.

Additionally or alternatively, precursor tube 92 can be stretched in radially outward directions 98, such as by blow molding, which increases the diameter and circumference of precursor tube 92. The increase in circumference results in stress that induces polymer molecule chains to have a preferential orientation in circumferential directions 100.

Figures 11, 12A, 12B, 12C:
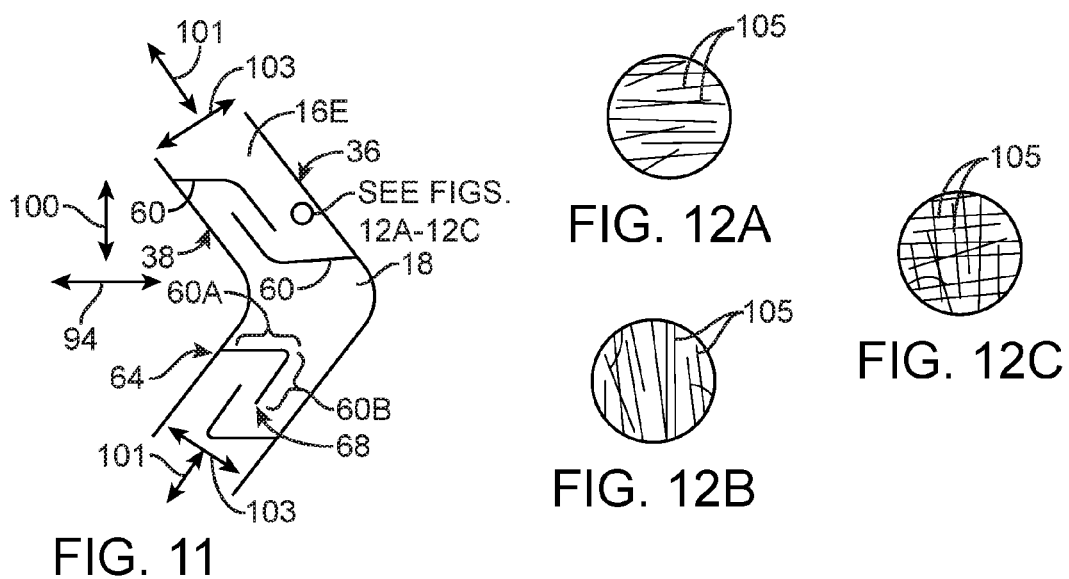
FIG. 11 shows a portion of a tubular scaffold with two adjacent bars that each has an elongation mechanism.
FIGS. 12A-12C are simplified representations of exemplary preferential orientation of polymer molecule chains.

Precursor tube 92 can be made according to a combination of processes, such as a combination of extrusion followed by blow molding, which can result in polymer molecule chains having a preferential biaxial orientation. With biaxial orientation, preferential orientation is in two directions. Preferential orientation in both the axial and the circumferential directions 94, 100 can provide desirable mechanical properties depending on the orientation of stent struts 14. For example, when the polymer molecule chains have a preferential orientation along the length of bar 16, tensile strength in the length direction of the bar will be greater than tensile strength in the transverse direction. FIG. 11 shows elongating bars 16E and hinges 18 in a manufactured state. Length directions of bars are indicated bar arrows 101. Transverse directions are indicated bar arrows 103.

FIGS. 12A-12C show simplified representations, in microscopic scale, of exemplary preferential orientation of polymer molecule chains 105 in bars 16E and hinges 18. In FIG. 12A, preferential orientation is uniaxial in axial directions 94, which are parallel to central axis 12 (FIG. 1) of the tubular scaffold. In FIG. 12B, preferential orientation is uniaxial in circumferential directions 100. In FIG. 12C, preferential orientation is biaxial in axial directions 94 and circumferential directions 100. At local areas of the tubular scaffold, axial directions 94 are perpendicular to circumferential directions 100.

Figures 13A, 13B, 13C:
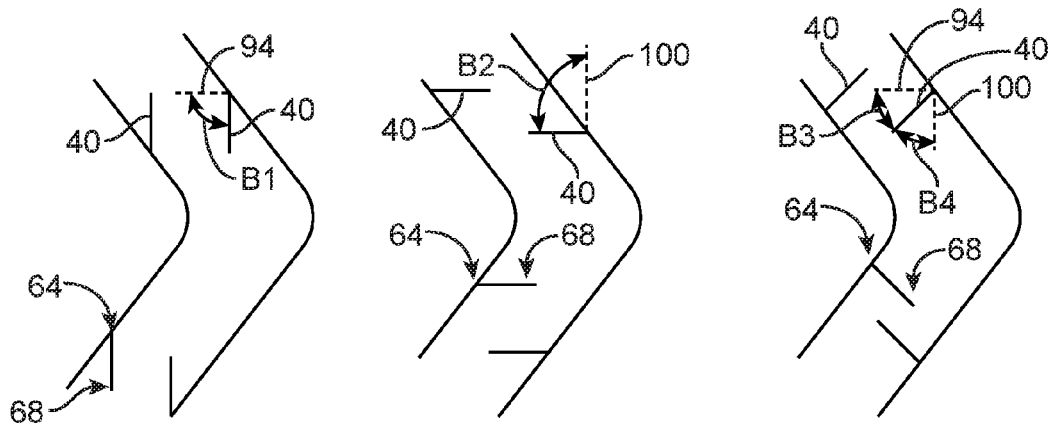
FIGS. 13A-13C show portions of tubular scaffolds with two adjacent bars that each have elongation mechanism.

In some embodiments, each cut 40 of a particular elongation mechanism 30 are orientated at a non-zero angle from the preferred orientation of polymer molecule chains at the cut. In FIG. 13A, preferred orientation is uniaxial in axial directions 94 as indicated in in FIG. 12A. Cuts 40 (more specifically, interior cut surfaces at starting end 64 and terminal end 68 of the cut) are orientated at angle B1 from axial directions 94.

In FIG. 13B, preferred orientation is uniaxial in circumferential directions 100 as in FIG. 12B. Cuts 40 (more specifically, interior cut surfaces at starting end 64 and terminal end 68 of the cut) are orientated at angle B2 from circumferential directions 100.

In FIG. 13C, preferred orientation is biaxial in axial directions 94 and circumferential directions 100 as in FIG. 12C. Cuts 40 (more specifically, interior cut surfaces at starting end 64 and terminal end 68 of the cut) are oriented at angle B3 from axial directions 94 and at angle B4 from circumferential directions 100.

Angles B1, B2, B3, and B4 are referred to as "separation angles" since they are the angles between a cut and the preferred orientations of polymer molecule chains located at the cut. The separation angles can be in the range from 20 degrees to 90 degrees, or from 30 degrees to 60 degrees, or from 40 degrees to 50 degrees.

It is believed that negative effects on tensile strength or ductility of bars 16E can be minimized by having cuts oriented as close as possible to perpendicular relative to the preferred orientation. Thus, it may be desirable to avoid alignment of cuts with the preferred orientation of polymer molecule chains. For example, when preferred orientation is uniaxial (e.g., FIGS. 13B and 13C), the separation angle (e.g., B1 and B2) can be in the range from 45 degrees to 90 degrees, or from 60 degrees to 90 degrees.

When preferred orientation is biaxial with each orientation being perpendicular to each other (e.g., FIG. 13C), making a cut perpendicular to one preferential orientation (e.g., orientation in axial directions 94) would result in the cut being parallel to the other preferential orientation (e.g. orientation in circumferential directions 100). Therefore, when preferred orientation is biaxial, it may be desirable to have cuts oriented at equal angles from both preferential orientations. For example, cuts 40 in FIG. 13C can be oriented such that separation angles B3 and B4 are both 45 degrees or in the range of 30 degrees to 60 degrees.

In FIGS. 13A-13C, each cut 40 consist of a single linear segment. A linear cut segment has cut interior surfaces that are flat planes. These cuts can be replaced with cuts that are non-linear and/or can have multiple linear segments, as shown in FIGS. 6 and 11. Cuts that are curved and/or that include multiple linear segments can help minimize alignment of cuts with the preferred orientation of polymer molecule chains. As indicated above, alignment of cuts with preferred orientation may reduce tensile strength or ductility of elongating bars 16E.

Referring again to FIG. 11, cut 60 includes of two linear cut segments 60A and 60B. Cut segment 60A is adjacent to starting end 64 of cut 60 and is parallel to axial directions 94. Cut segment 60B is adjacent to terminal end 68 of cut 60 and is parallel to first and second side surfaces 36, 38. When elongating bar 16E of FIG. 12 has the uniaxial preferential orientation of FIG. 12B, cut segment 60B has the advantage of not being aligned with the preferential orientation. However, cut segment 60A would be aligned with the preferential orientation.

When elongating bar 16E of FIG. 11 has the biaxial preferential orientation of FIG. 12C, cut segment 60B has the advantage of not being aligned with any of the preferential orientations (i.e., not aligned with preferential orientations in axial and circumferential 94, 100). However, cut segment 60A would be aligned with one of the preferential orientations (i.e., aligned with preferential orientation in axial directions 94).

Embodiments of the present invention include one or more elongating bars 16E each having elongation mechanism 30 that has at least one linear cut segment that is not aligned with any preferential orientation of polymer molecule chains of the elongating bar. For example, at least one linear cut segment of the cut is at least 10 degrees (or at least 20 degrees) from the preferential orientation in a uniaxial oriented polymer, or at least 10 (or at least 20 degrees) degrees from both preferential orientations in a biaxial oriented polymer.

It is believed that stress during stent deployment would be higher at cut segment 60B (more specifically, highest at terminal end 68 of the cut) as compared to other segments of the cut. Thus, it may be advantageous to put priority on maximizing the separation angle of cut segments adjacent to terminal end 68 as opposed to starting end 64. Embodiments of the present invention include one or more elongating bars 16E each having elongation mechanism 30 that has a terminal cut segment at terminal end 68 of the cut. The terminal cut segment is not aligned with any preferential orientation of polymer molecule chains of the elongating bar. For example, the terminal cut segment is at least 10 degrees (or at least 20 degrees) from the preferential orientation in a uniaxial oriented polymer, or at least 10 degrees (or at least 20 degrees) from both preferential orientations in a biaxial oriented polymer. An example of a terminal cut segment can be terminal cut segment 102 in FIG. 6 and segment 60B in FIG. 11. Terminal cut segment 102 can be linear cut segments and can have a length (measured at the abluminal or luminal surface) that is at least 10% or at least 20% of bar transverse width 46.

Figure 14A:
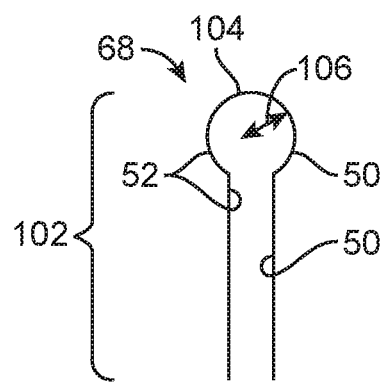
FIGS. 14A and 14B show exemplary rounded geometries at terminal ends of cuts of an elongation mechanism.
Figure 14B:
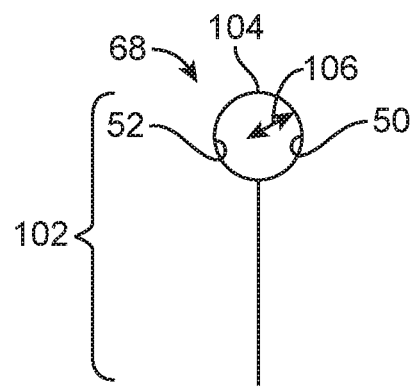

FIGS. 14A, 14B, 15A, and 15C show exemplary terminal cut segments 102 that can be implemented in any of the embodiments herein. Terminal cut segments 102 are shown when the tubular scaffold is in a manufactured state. As mentioned above, it is believed stress during stent deployment can be highest at terminal end 68 of a cut as compared to other parts of the cut. In FIGS. 14A and 14B, terminal end 68 is formed with a radius or rounded geometry 104. Rounded geometry 104 can help reduce the concentration of stress at terminal end 68 during stent deployment as compared to a terminal end with a sharp geometry. Rounded geometry 104 can have radius 106 that is at least 2% of bar transverse width 46. Alternatively, radius 106 can be from 2% to 5% or from 2% to 10% of cut transverse width 46.

In FIG. 14A, cut surfaces 50, 52 do not contact each other when the tubular scaffold is in the manufactured state, and surfaces 50, 52 spread further apart at rounded geometry 104.

In FIG. 14B, cut surfaces 50, 52 outside rounded geometry 104 contact each other when the tubular scaffold is in the manufactured state. Within rounded geometry 104, surfaces 50, 52 do not contact each other when the tubular scaffold is in the manufactured state.

Figure 15A:
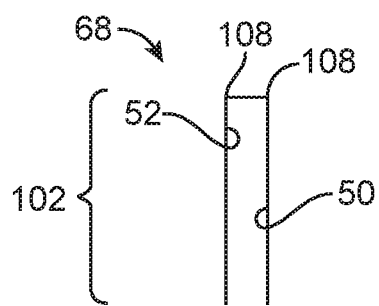
FIGS. 15A and 15B show exemplary sharp geometries at terminal ends of cuts of an elongation mechanism.

In FIG. 15A, cut surfaces 50 and 52 do not do not contact each other when the tubular scaffold is in the manufactured state. At terminal end 68, abrupt corners create sharp geometries 108.

Figure 15B:
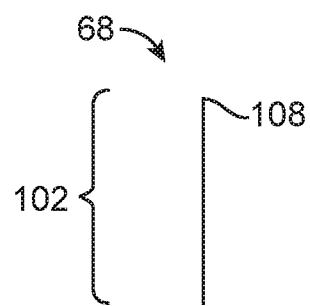

In FIG. 15B, cut surfaces 50 and 52 contact each throughout terminal cut segment 102 when the tubular scaffold is in the manufactured state. The ends of cut surfaces 50, 52 at terminal end 68 create sharp geometry 108.

In any of the above described embodiments, stent 10 can be made of core metal material instead of a core polymer material. A stent made of a core metal material is called metal stent 10 in the description below. A stent made of a core polymer material is called polymer stent 10 in the description below.

Examples of core metal material include without limitation cobalt chromium alloy (e.g., ELGILOY), stainless steel (316L), high nitrogen stainless steel, e.g., BIODUR 108, cobalt chrome alloy L-605, "MP35N," "MP2ON," ELASTINITE (Nitinol), tantalum, nickel-titanium alloy, platinum-iridium alloy, gold, magnesium, or combinations thereof. "MP35N" and "MP2ON" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP2ON" consists of 50% cobalt, 20% nickel, 20% chromium, and 10% molybdenum.

For example, precursor tube 92 can be made of core metal material 80, and then cut to form bars 16, hinges 18, and links 22 that define the tubular scaffold of metal stent 10. Optionally, a coating process can be performed to apply surface coating 78 on core metal material 80 as previously described for a core polymer material. A cutting process for making elongation mechanism 30 can be performed in the matter as previously described for a core polymer material to provide results as shown FIGS. 9A-9C and any other figures above.

Elongation mechanism 30 of metal stent 10 can allow for positive remodeling of the anatomical lumen. For example, metal stent 10 can be deployed to complete the first phase of deployment as previously described for polymer stent 10. Next, catheter 24 is withdrawn while metal stent 10 remains at the first phase of deployment (e.g., FIG. 2C). Elongation mechanisms 30 are in a folded or compressed configuration and thus prevent or inhibit metal stent 10 from recoiling to a diameter less than outer diameter 26C. Over time, metal stent 10 can become embedded within tissue growth at the anatomical lumen. Without any elongation mechanisms, a conventional metal stent could act as a cage when it becomes embedded and thus inhibit or prevent positive remodeling of the anatomical lumen, which involves allowing the anatomical lumen to enlarge naturally. Elongation mechanisms 30 of metal stent 10 is capable of moving from its folded or compressed configuration (e.g., FIG. 3C and FIG. 4C) to an unfolded or elongated configuration (e.g., FIGS. 4C and 4D) and could allow for positive remodeling to occur.

The potential benefit of elongation mechanisms 30 with respect to positive remodeling of the anatomical lumen also apply to polymer stent 10. For example, polymer stent 10 can be implanted only to the first phase deployment as described above for metal stent 10. Even if polymer stent 10 begins to resorb in about six months after implantation, for example, elongation mechanisms 30 of polymer stent 10 can allow for positive remodeling to occur before the sixth month.

As a further example, polymer stent 10 can be implanted to the second phase of deployment as previously described in connection with FIG. 2D. After removal of catheter 24, polymer stent 10 can return to diameter 26C of FIG. 2C. Afterwards, elongation mechanisms 30 of polymer stent 10 can allow for positive remodeling to occur before polymer 10 completely degrades.

In other embodiments, an adhesive can be applied to cut interior surfaces 50, 52 of polymer stent 10 and metal stent 10. Additionally or alternatively, the adhesive can be applied on abluminal surface 32 and/or luminal surface 24 above cut. For example, the adhesive can fill the empty space between cut interior surfaces 50, 52 shown in FIGS. 5, 6, 9A and 9B. The adhesive can help keeps pivots 54 and fingers 56 from unfolding, and keeps elongation mechanisms 30 stable during crimping and during the first phase of deployment. After a few days after implantation or after a few months, the adhesive can degrade and loose its ability to keep pivots 54 and fingers 56 from unfolding. After the adhesive degrades, elongation mechanisms 30 may allow for positive remodeling to occur. A non-limiting example of a degradable adhesive is amorphous poly-DL-lactide (PDLLA).

The adhesive can include natural polymeric materials and/or synthetic polymeric materials. Examples of adhesives, for use as described above, include without limitation those described in U.S. Patent Application Publication No. 2014/0074219.

Figure 19:
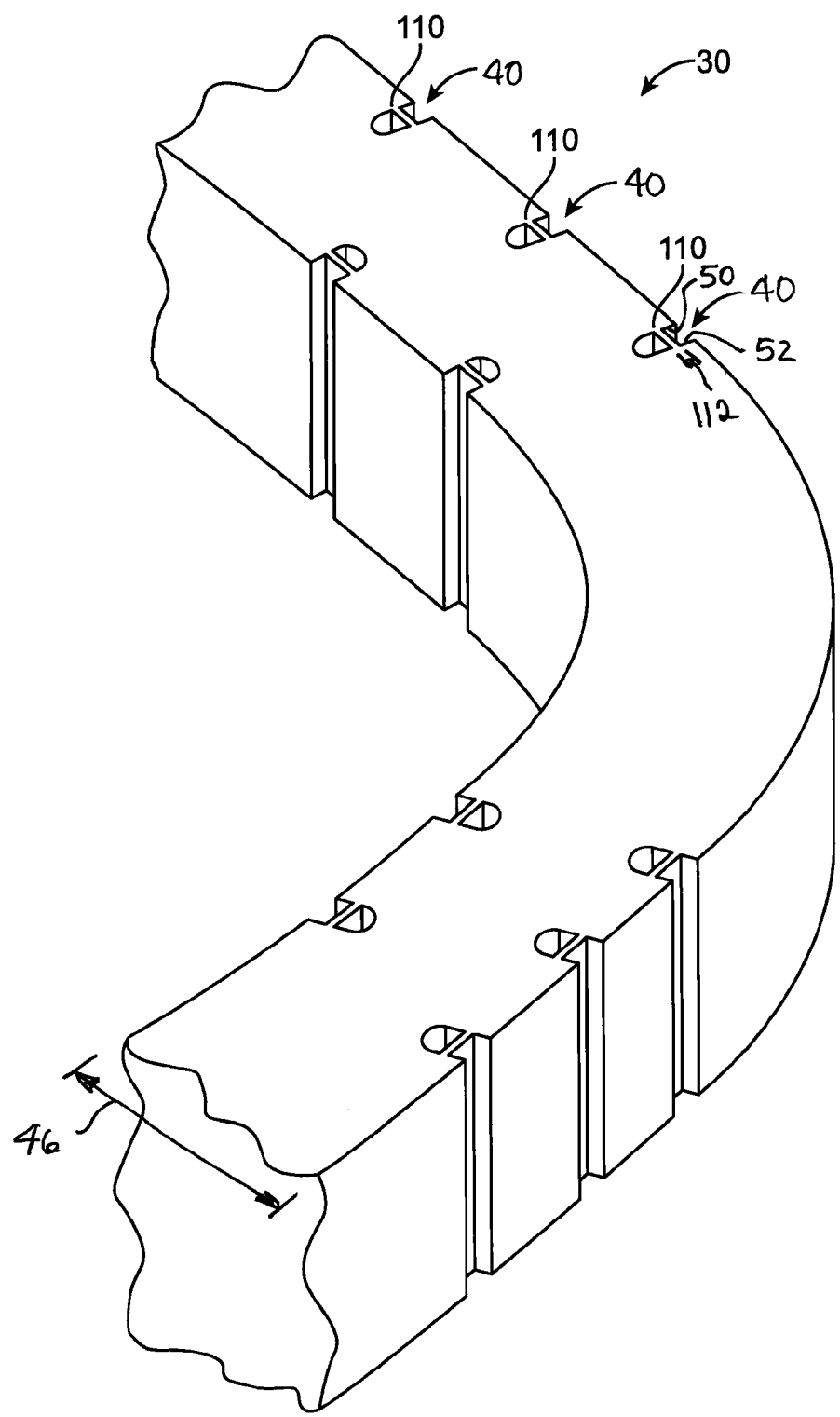
FIGS. 19 and 20 are perspective views showing elongation mechanisms having discontinuous cuts.
Figure 20:
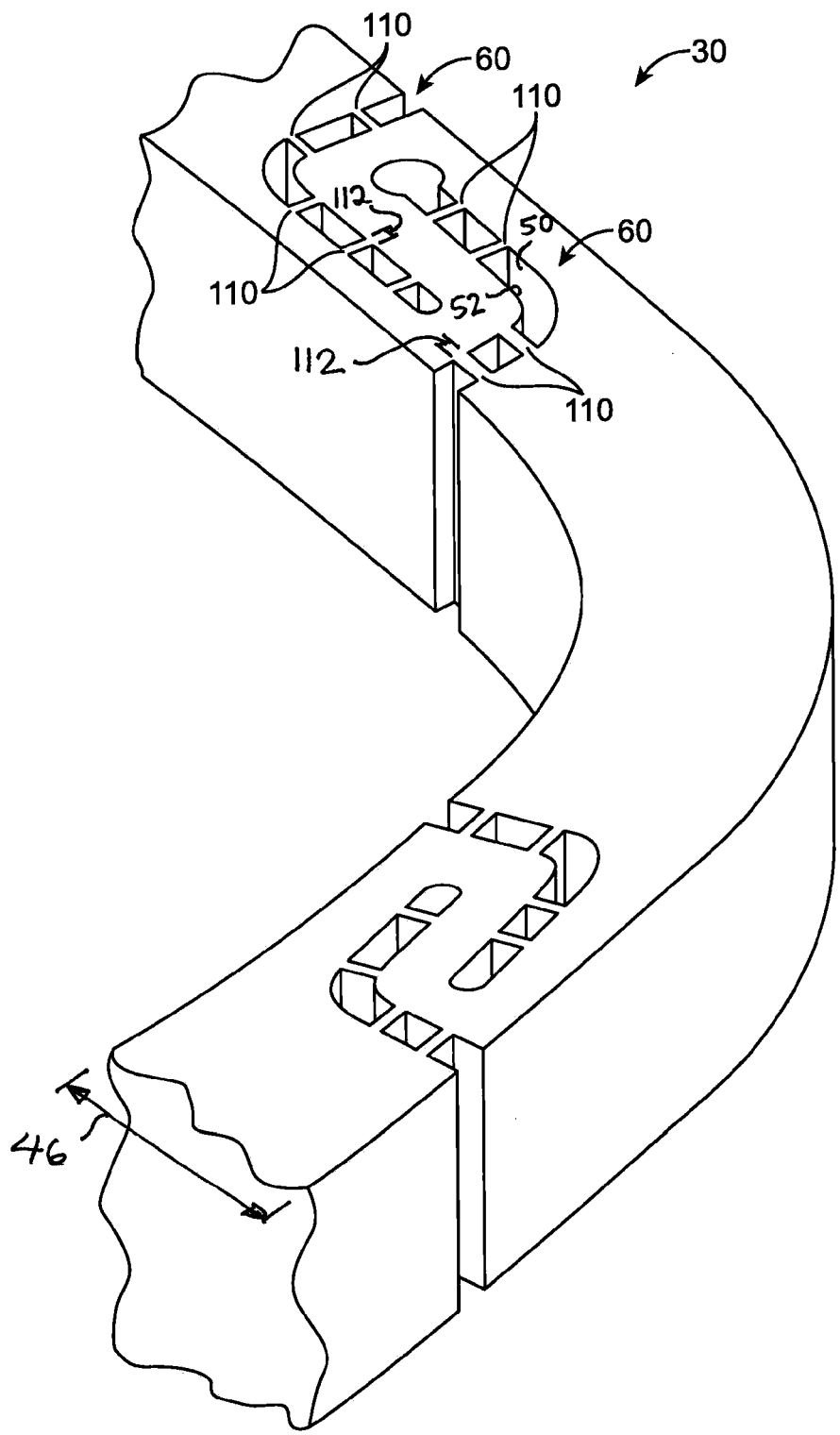

As shown in FIGS. 3A, 4A, 5, 6, 11, and 13A-13C, cuts 40, 60 can be continuous from the starting end 64 to terminal end 68 of the cut. Additionally or alternatively, any one or more of those cuts can be discontinuous. FIGS. 19 and 20 show discontinuous cuts 40, 60. Discontinuous cuts 40 are defined by one or more bridges 110 of core material, which can be a core polymer material or a core metal material. Bridges 110 stabilize cuts 40, 60 during crimping and the phrase phase of expansion. Each bridges 110 connects cut interior surface 50 to cut interior surface 52. Each bridge 112 has a width 112 that is less than 10% or less than 5% of bar transverse width 46. The smaller width of the bridges enables the bridges to break apart during second phase expansion.

Any one or more of the cuts 40, 60 previously described optionally includes a vasodilator agent contained between cut interior surfaces 50, 52. The vasodilator agent is released when cuts 40, 60 open, such as during second phase deployment (which occur rapidly by inflation of a catheter portion of a balloon) and/or during positive remodeling of the anatomical lumen (which can occur over longer periods of time). The vasodilator agent causes relaxation of smooth muscle cells within the walls of the anatomical lumen and facilitates widening or expansion of the anatomical lumen.

Examples of vasodilator agents include without limitation nitrogen oxide and adenosine. Additional examples include without limitation the vasodilator agents mentioned in US Patent Publication No. 2008/0138377.

The vasodilator agent can occupy the gap shown in FIG. 9A between interior surfaces 50, 52 of the cut. A relatively small or negligible amount of vasodilator agent can be released prior to deployment of stent 10/The amount is small or negligible due to the closed or folded configuration of the cuts. A greater amount of vasodilator is released when the cuts open.

In FIG. 9B, the vasodilator agent can occupy the gap between interior surfaces 50, 52. The vasodilator agent is encapsulated and sealed within surface coating 78 which contains no vasodilator agent. Surface coating 78 inhibits or prevents release of any vasodilator agent, such as when stent 10 is being passed through an anatomical lumen before it has reached the intended area where the stent is to be deployed. When the cuts open, surface coating 78 breaks at or near the cuts, which allows for release of the vasodilator agent.

In FIG. 9C, the vasodilator agent can be carried within surface coating 78, in which case the vasodilator agent is present on the outer surfaces of stent 10 as well as contained between interior surfaces 50, 52 of the cuts. The vasodilator agent elutes out of surface coating 78 after implantation. A greater amount of vasodilator is released when the cuts open.

EXAMPLES

Finite element models of two bars and a hinge were developed based on a core biaxial poly-L lactide polymer material. A baseline model had no cuts. A first comparison model (called "¼ cut" model in FIG. 16) had linear cuts 40 that had cut transverse depth 48 that was 25% of bar transverse width 46. A second comparison model (called "½ cut" model in FIGS. 17 and 18) had linear cuts 40 that had cut transverse depth 48 that was 50% of bar transverse width 46. Finite element analysis provided a predicted radial strength of 939 mmHg for the baseline model, 898 mmHg (about a 4% reduction) for the first comparison model, and 577 mmHg (about 39% reduction) for the second comparison model.

Second phase deployment from a stent outer diameter of 3.7 mm to 5 mm was simulated and the maximum principal stress at various parts of the stent was determined versus diameter. Referring to FIG. 1, reference numeral 18U designates a U-type hinge where two bars 16 meet without link 22, and reference numeral 18Y designates a Y-type hinge where two bars 16 and link 22 meet. For the baseline model, maximum principal stress was greatest at Y-type hinges. Therefore, the maximum principal stress at Y-type hinges of the baseline model is used as a basis of comparison with the first and second comparison models.

Figure 16:
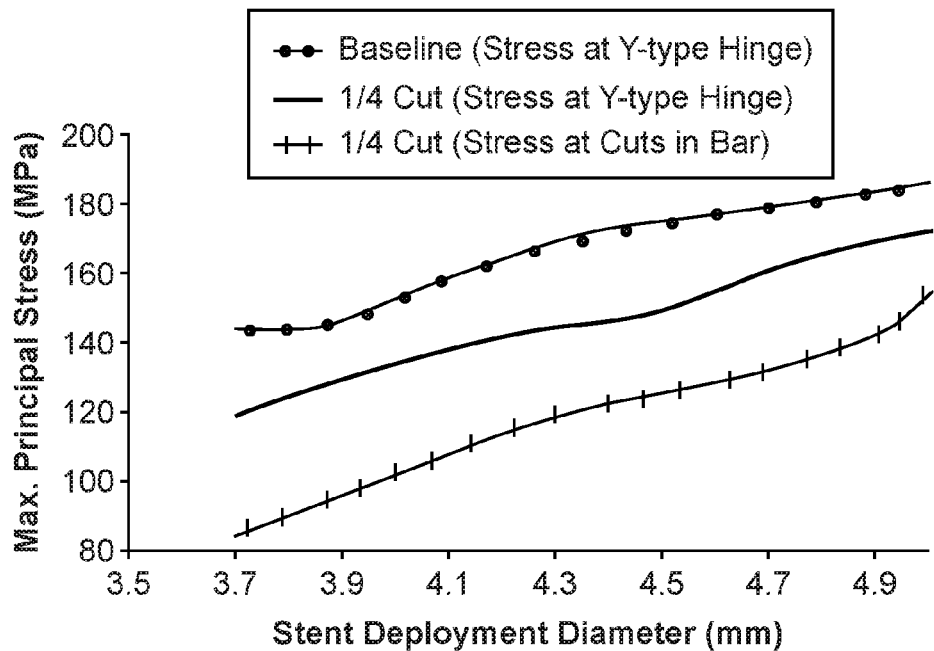
FIGS. 16-18 are graphs showing comparisons between a baseline finite element model having no elongation mechanism with other finite element models having various elongation mechanisms.

FIG. 16 shows the maximum principal stress at Y-type hinges of the baseline model compared to the maximum principal stresses for the first comparison model (¼ cut model). Maximum principal stress increases as stent outer diameter increases from 3.7 mm to 5 mm. Notably, stress at Y-type hinges of the ¼ cut model are lower than those at Y-type hinges of the baseline model. Maximum principal stress at Y-type hinges was reduced by about 14% and indicates that the ¼ cut model would be capable of greater expansion before reaching the same level of stress experienced by the baseline model. For instance, about 150 MPa is reached when the baseline model is deployed to slightly above 3.9 mm diameter, whereas 150 MPa is not reached by the ¼ cut model until it deployed to about 4.5 mm diameter. Maximum principal stress along the bars (more specifically, at the cuts) are below those at Y-type hinges of the baseline and ¼ cut models. Thus, the ¼ cut model appear to provide a benefit in reducing maximum principal stress as compared baseline (no cuts) without resulting in excessive stress at the cuts.

Figure 17:
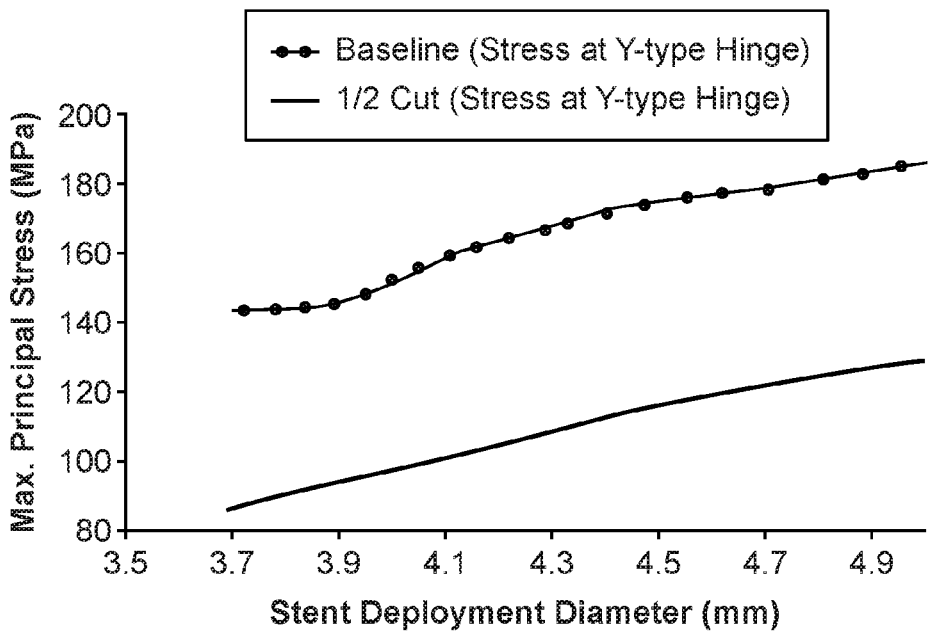
Figure 18:
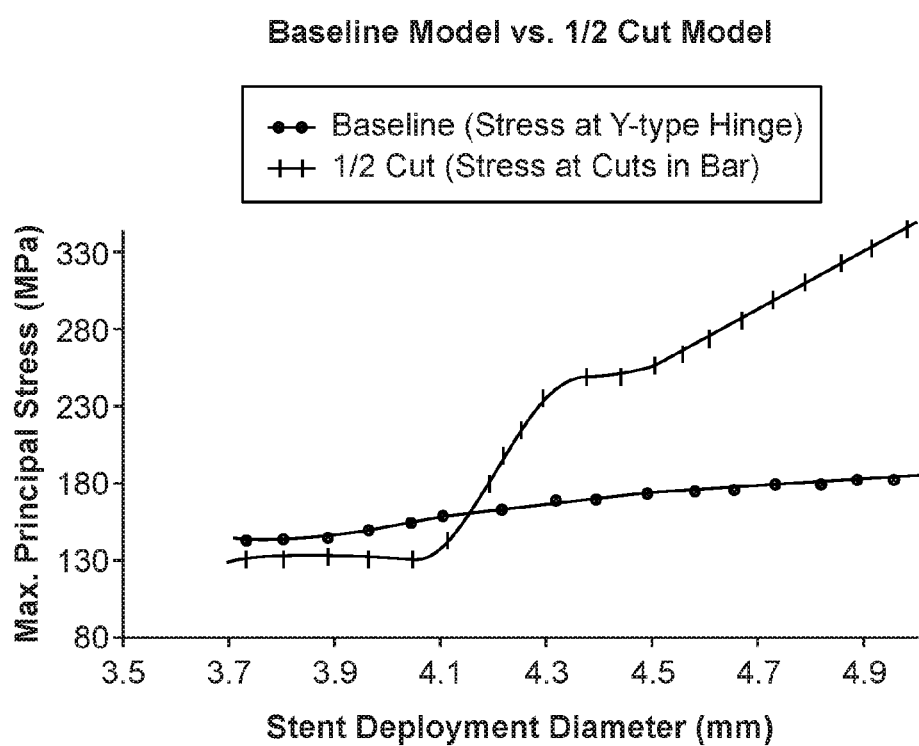

FIG. 17, which is on the same scale as FIG. 16, shows the maximum principal stress at Y-type hinges of the baseline model compared to the maximum principal stress at Y-type hinges of the second comparison model (½ cut model). Stress at Y-type hinges of the ½ cut model are much lower than those at Y-type hinges of the baseline and ¼ cut models. However, as shown in FIG. 18 when the ½ cut model is beyond about 4.2 mm diameter, maximum principal stress along the bars (more specifically, at the cuts) of the ½ cut model exceeds the maximum principal stress at Y-type hinges of the baseline model. Thus, the ½ cut model appears to result in excessive stress at the cuts.

It is contemplated that improvements in both comparison models may be achieved with rounded geometries at terminal ends of cuts and by considering separation angles between cuts and preferred orientation of polymer molecule chains.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A stent comprising:
a plurality of rings, each ring including an alternating series of bars and hinges, each hinge configured to bend inward to allow the ring to be radially compressed from a manufactured state to a crimped state, each hinge configured to bend outward to allow the ring to radially expand from the crimped state to a deployed state; and
a plurality of links connecting the rings together,
wherein the rings and links form a tubular scaffold having a central axis,
wherein at least one of the bars includes an elongation mechanism having a folded configuration when the ring is in the manufactured state and the crimped state and having an unfolded configuration when the ring is in the deployed state, and
wherein the elongation mechanism includes a discontinuous cut formed into the bar, the bar is made of a core material that forms a bridge across the discontinuous cut.

2. The stent of claim 1, wherein at least one of the bars in each of the rings includes an elongation mechanism.

3. The stent of claim 1, wherein at least two of the bars in the same ring include an elongation mechanism.

4. A stent comprising:
a plurality of rings, each ring including an alternating series of bars and hinges, each hinge configured to bend inward to allow the ring to be radially compressed from a manufactured state to a crimped state, each hinge configured to bend outward to allow the ring to radially expand from the crimped state to a first deployed state and further radially expand to a second deployed state; and
a plurality of links connecting the rings together,
wherein the rings and links form a tubular scaffold having a central axis, and
wherein at least one of the bars includes a plurality of pivots and fingers having a folded configuration when the ring is in a crimped state, the pivots and fingers are configured to remain in the folded configuration when the ring is radially expanded from the crimped state to the first deployed state, and are configured to unfold from the folded configuration when the ring radially expands from the first deployed state to the second deployed state, wherein the pivots and fingers are formed by cuts in the side surfaces of the at least one bar.

5. A stent comprising:

a plurality of rings, each ring including an alternating series of bars and hinges, each hinge configured to bend inward to allow the ring to be radially compressed from a manufactured state to a crimped state, each hinge configured to bend outward to allow the ring to radially expand from the crimped state to a first deployed state and further radially expand to a second deployed state; and a plurality of links connecting the rings together, wherein the rings and links form a tubular scaffold having a central axis, and wherein at least one of the bars includes a plurality of pivots and fingers having a folded configuration when the ring is in a crimped state, the pivots and fingers are configured to remain in the folded configuration when the ring is radially expanded from the crimped state to the first deployed state, and are configured to unfold from the folded configuration when the ring radially expands from the first deployed state to the second deployed state, wherein the bar is made of a core material, and the pivots and fingers form an S-shape of core material.

6. A stent comprising:

a plurality of rings, each ring including an alternating series of bars and hinges, each hinge configured to bend inward to allow the ring to be radially compressed from a manufactured state to a crimped state, each hinge configured to bend outward to allow the ring to radially expand from the crimped state to a first deployed state and further radially expand to a second deployed state; and a plurality of links connecting the rings together, wherein the rings and links form a tubular scaffold having a central axis, and wherein at least one of the bars includes a plurality of pivots and fingers having a folded configuration when the ring is in a crimped state, the pivots and fingers are configured to remain in the folded configuration when the ring is radially expanded from the crimped state to the first deployed state, and are configured to unfold from the folded configuration when the ring radially expands from the first deployed state to the second deployed state, wherein the core material is a polymer or a metal.

7. A stent comprising:

a plurality of rings, each ring including an alternating series of bars and hinges, each hinge configured to bend inward to allow the ring to be radially compressed from a manufactured state to a crimped state, each hinge configured to bend outward to allow the ring to radially expand from the crimped state to a first deployed state and further radially expand to a second deployed state; and a plurality of links connecting the rings together, wherein the rings and links form a tubular scaffold having a central axis, and wherein at least one of the bars includes a plurality of pivots and fingers having a folded configuration when the ring is in a crimped state, the pivots and fingers are configured to remain in the folded configuration when the ring is radially expanded from the crimped state to the first deployed state, and are configured to unfold from the folded configuration when the ring radially expands from the first deployed state to the second deployed state, wherein the ring is configured to provide support to an anatomical lumen when the ring is in the first deployed state.

* * * * *